(12) United States Patent
Iwamura et al.

(10) Patent No.: US 11,488,297 B2
(45) Date of Patent: Nov. 1, 2022

(54) MEDICAL INFORMATION PROCESSING APPARATUS AND MEDICAL INFORMATION PROCESSING SYSTEM

(71) Applicant: CANON MEDICAL SYSTEMS CORPORATION, Otawara (JP)

(72) Inventors: Taisuke Iwamura, Utsunomiya (JP); Keita Mitsumori, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 159 days.

(21) Appl. No.: 16/716,939

(22) Filed: Dec. 17, 2019

(65) Prior Publication Data

US 2020/0193595 A1  Jun. 18, 2020

(30) Foreign Application Priority Data

Dec. 18, 2018 (JP) .............................. JP2018-236589

(51) Int. Cl.
| | |
|---|---|
| *G06T 7/00* | (2017.01) |
| *G16H 10/60* | (2018.01) |
| *G16H 30/40* | (2018.01) |
| *G06T 1/20* | (2006.01) |
| *G16H 50/50* | (2018.01) |

(52) U.S. Cl.
CPC .............. *G06T 7/0012* (2013.01); *G06T 1/20* (2013.01); *G16H 10/60* (2018.01); *G16H 30/40* (2018.01); *G16H 50/50* (2018.01); *G06T 2207/20081* (2013.01); *G06T 2207/20084* (2013.01); *G06T 2207/30004* (2013.01)

(58) Field of Classification Search
CPC ..................... G06T 7/0012; G06T 1/20; G06T 2207/20081; G06T 2207/30004; G06T 2207/20084; G16H 10/60; G16H 30/40; G16H 50/50; G16H 30/20; G16H 50/70; G16H 50/20
USPC .......................................................... 382/128
See application file for complete search history.

(56) References Cited

U.S. PATENT DOCUMENTS

| | | | | |
|---|---|---|---|---|
| 2013/0290826 | A1* | 10/2013 | Niwa ..................... | G16H 30/20 |
| | | | | 715/230 |
| 2017/0262598 | A1* | 9/2017 | Petkov .................. | G06T 15/005 |
| 2018/0137244 | A1* | 5/2018 | Sorenson ............... | G16H 30/20 |

(Continued)

FOREIGN PATENT DOCUMENTS

| | | |
|---|---|---|
| JP | 2012-221365 A | 11/2012 |
| JP | 2013-132514 A | 7/2013 |

(Continued)

*Primary Examiner* — Van D Huynh
(74) *Attorney, Agent, or Firm* — Oblon, McClelland, Maier & Neustadt, L.L.P.

(57) ABSTRACT

A medical information processing apparatus according to an embodiment includes: a memory storing therein a trained model provided with a function to specify, on the basis of input information including a medical image and medical examination information related to the medical image, at least one selected from between a relevant image relevant to the medical image and an image processing process performed on the basis of the medical image; and processing circuitry configured to give an evaluation to at least one selected from between the relevant image and the image processing process specified by the trained model.

18 Claims, 7 Drawing Sheets

(56) References Cited

U.S. PATENT DOCUMENTS

2018/0144466 A1* 5/2018 Hsieh .................... G06T 7/0012
2019/0295248 A1* 9/2019 Nakamura ............. G06V 20/00

FOREIGN PATENT DOCUMENTS

| JP | 2015-160085 A | 9/2015 |
| JP | 2017-097654 A | 6/2017 |

* cited by examiner

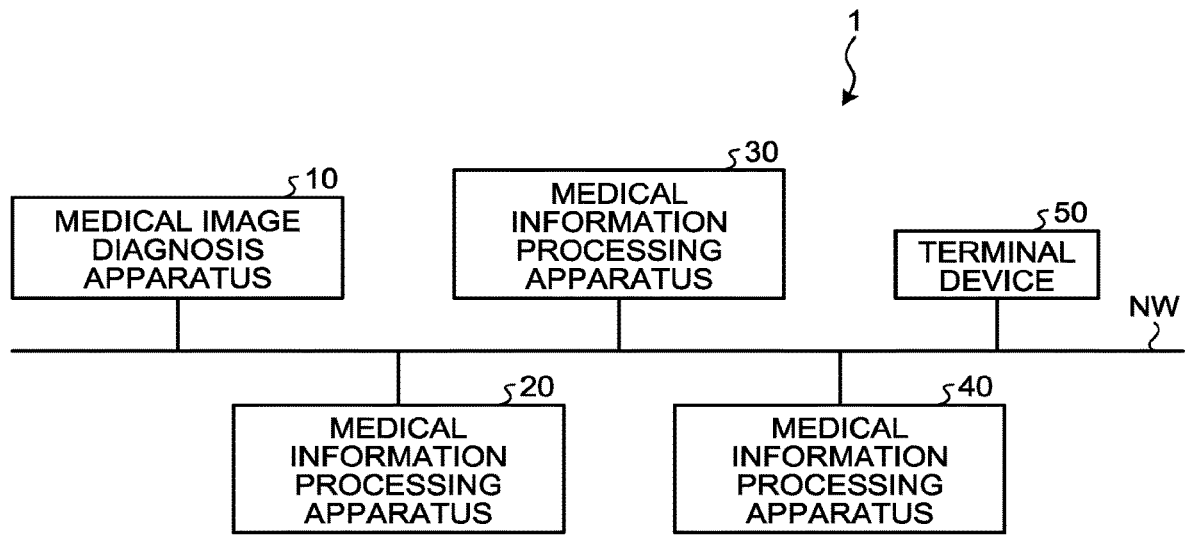
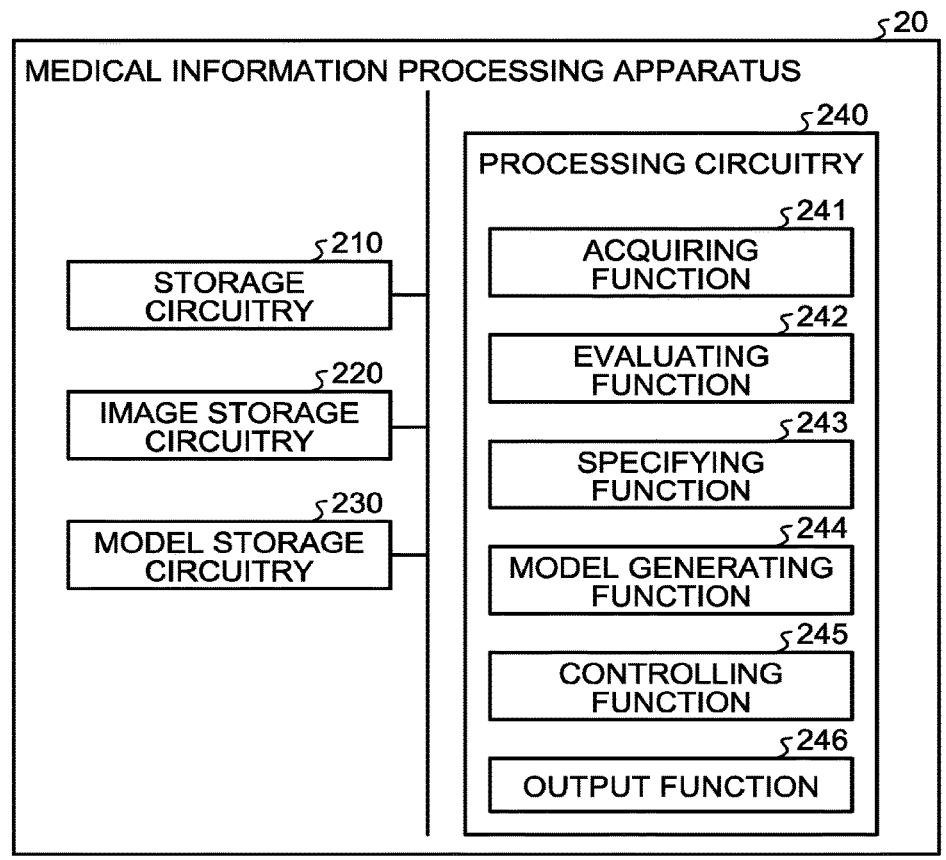

FIG.8

| | |
|---|---|
| NO EXCESS OR INSUFFICIENCY | +2 |
| EXCESS | +1 |
| DELAY | -1 |
| INSUFFICIENCY | -2 |

MEDICAL INFORMATION PROCESSING APPARATUS AND MEDICAL INFORMATION PROCESSING SYSTEM

CROSS-REFERENCE TO RELATED APPLICATIONS

This application is based upon and claims the benefit of priority from Japanese Patent Application No. 2018-236589, filed on Dec. 18, 2018; the entire contents of which are incorporated herein by reference.

FIELD

Embodiments described herein relate generally to a medical information processing apparatus and a medical information processing system.

BACKGROUND

For image interpretation, in addition to medical images acquired from a patient during a medical examination, other various images are used for reference purposes. An image interpreting doctor is thereby able to prepare an observation report more properly than when interpreting images by using only the acquired medical images. For this reason, a workflow from the acquisition to the interpretation of the medical images includes a step of bringing the reference-purpose images into a displayable state, in addition to a step of bringing the acquired medical images into a displayable state.

BRIEF DESCRIPTION OF THE DRAWINGS

FIG. 1 is a block diagram illustrating an exemplary configuration of a medical information processing system according to a first embodiment;

FIG. 2 is a block diagram illustrating an exemplary configuration of a medical information processing apparatus according to the first embodiment;

FIG. 8 is a table illustrating examples of an evaluation according to the first embodiment.

DETAILED DESCRIPTION

Figure 3:
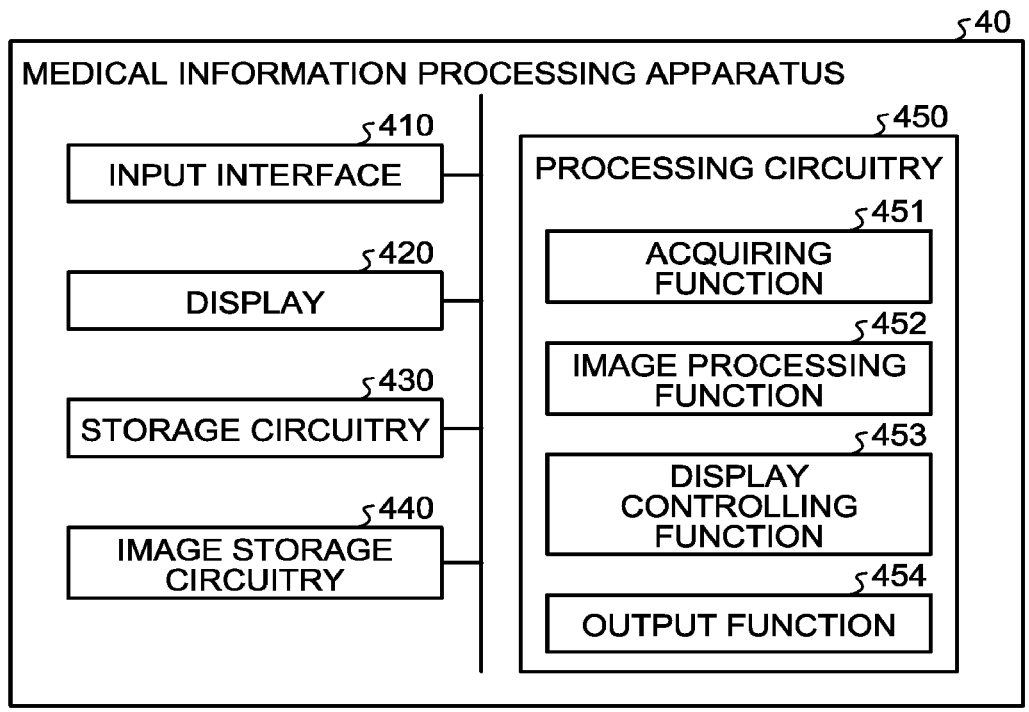
FIG. 3 is a block diagram illustrating an exemplary configuration of another medical information processing apparatus according to the first embodiment.

A medical information processing apparatus comprises a memory and processing circuitry. The memory stores therein a trained model provided with a function to specify, on a basis of input information including a medical image and medical examination information related to the medical image, at least one selected from between a relevant image relevant to the medical image and an image processing process performed on a basis of the medical image. The processing circuitry is configured to give an evaluation to at least one selected from between the relevant image and the image processing process specified by the trained model.

Exemplary embodiments of the medical information processing apparatus and a medical information processing system will be explained in detail below, with reference to the accompanying drawings.

To begin with, a first embodiment will be explained. The first embodiment will be explained by using a medical information processing system 1 illustrated in FIG. 1 as an example. FIG. 1 is a block diagram illustrating an exemplary configuration of the medical information processing system 1 according to the first embodiment.

As illustrated in FIG. 1, the medical information processing system 1 according to the first embodiment includes a medical image diagnosis apparatus 10, a medical information processing apparatus 20, another medical information processing apparatus 30, yet another medical information processing apparatus 40, and a terminal device 50. The medical image diagnosis apparatus 10, the medical information processing apparatus 20, the medical information processing apparatus 30, the medical information processing apparatus 40, and the terminal device 50 are connected to one another via a network NW.

The medical image diagnosis apparatus 10 is an apparatus configured to acquire medical images from a patient. The images processed as data may be referred to as image data. The medical image diagnosis apparatus 10 is configured to acquire medical image data from the patient and to output the acquired medical image data to one of the medical information processing apparatus 20 and the medical information processing apparatus 30. For example, the medical image diagnosis apparatus 10 may be an X-ray Computed Tomography (CT) apparatus, an X-ray diagnosis apparatus, an ultrasound diagnosis apparatus, a Single Photon Emission Computed Tomography (SPECT) apparatus, a SPECT-CT apparatus in which a SPECT apparatus and an X-ray CT apparatus are integrally formed, or the like. Although FIG. 1 illustrates only the single medical image diagnosis apparatus 10, the medical information processing system 1 may include two or more medical image diagnosis apparatuses 10.

For example, when the medical image diagnosis apparatus 10 is an X-ray CT apparatus, the medical image diagnosis apparatus 10 is configured to acquire projection data by performing a CT scan on the patient. Subsequently, the medical image diagnosis apparatus 10 is configured to generate CT image data (a plurality of tomographic images) on the basis of the projection data. More specifically, the medical image diagnosis apparatus 10 reconstructs CT image data by performing a reconstructing process that uses a filter correction back projection method, an approximate reconstruction method, or the like, on the projection data. In this situation, the CT image data is an example of the medical image data. Further, the medical image diagnosis apparatus 10 is configured to output the generated CT image data to the medical information processing apparatus 20.

The medical information processing apparatus 20 is an apparatus configured to save therein the medical image data acquired by the medical image diagnosis apparatus 10. For example, the medical information processing apparatus 20 is configured to acquire the medical image data from the medical image diagnosis apparatus 10 via the network NW and to store the acquired medical image data into storage circuitry provided inside or outside the apparatus. For example, the medical information processing apparatus 20 is realized by using a computer device such as a server apparatus. In one example, the medical information processing apparatus 20 is an image server provided in a Picture Archiving and Communication System (PACs).

Further, the medical information processing apparatus 20 is configured to acquire, from the medical information processing apparatus 30, relevant image data relevant to the medical image data acquired from the medical image diagnosis apparatus 10. Further, the medical information processing apparatus 20 is configured to output the medical image data acquired from the medical image diagnosis apparatus 10 to the medical information processing apparatus 40. Further, the medical information processing apparatus 20 is configured to acquire medical image data resulting from image processing processes performed by the medical information processing apparatus 40, from the medical information processing apparatus 40. Further, the medical information processing apparatus 20 is configured to output image data corresponding to a request from the terminal device 50, to the terminal device 50. Processes performed by the medical information processing apparatus 20 will be explained later.

The medical information processing apparatus 30 is an apparatus configured to save therein medical image data acquired by the medical image diagnosis apparatus 10. For example, the medical information processing apparatus 30 is configured to acquire the medical image data from the medical image diagnosis apparatus 10 via the network NW and to store the acquired medical image data into storage circuitry provided inside or outside the apparatus. In this situation, the medical information processing apparatus 30 saves therein the medical image data that is of a different type from the medical image data stored in the medical information processing apparatus 20. In one example, the medical information processing apparatus 20 saves therein still images such as CT image data or the like, whereas the medical information processing apparatus 30 saves therein moving images such as ultrasound image data or the like. For example, the medical information processing apparatus 30 is realized by using a computer device such as a server apparatus. In one example, the medical information processing apparatus 30 is an image server provided in a PACS.

The medical information processing apparatus 40 is configured to perform various types of image processing processes on the basis of the medical image data acquired by the medical image diagnosis apparatus 10. In one example, the medical information processing apparatus 40 is configured to generate three-dimensional image data on the basis of the CT image data (the plurality of tomographic images) and to further generate two-dimensional image data based on the three-dimensional image data. In another example, the medical information processing apparatus 40 is configured to perform an analyzing process based on the medical image data acquired by the medical image diagnosis apparatus 10. The image processing processes performed by the medical information processing apparatus 40 will be explained later.

The terminal device 50 is a device configured to present an image interpreting doctor with various types of image data. The terminal device 50 is configured to acquire the image data from the medical information processing apparatus 20 in response to an input operation received from the image interpreting doctor and to cause a display device to display the acquired image data. In other words, the medical information processing apparatus 20 keeps various types of image data in a displayable state, so that the terminal device 50 causes the display device to display the image data acquired from the medical information processing apparatus 20. For example, the terminal device 50 presents the image interpreting doctor with the medical image data acquired by the medical image diagnosis apparatus 10. In other words, by using the terminal device 50, the image interpreting doctor interprets the medical image data. For example, the terminal device 50 is realized by using a personal computer (PC), a tablet PC, or the like operated by the image interpreting doctor.

Next, a configuration of the medical information processing apparatus 20 will be explained, with reference to FIG. 2. FIG. 2 is a block diagram illustrating an exemplary configuration of the medical information processing apparatus 20 according to the first embodiment. For example, as illustrated in FIG. 2, the medical information processing apparatus 20 includes storage circuitry 210, image storage circuitry 220, model storage circuitry 230, and processing circuitry 240.

The storage circuitry 210 is configured to store therein programs that correspond to various types of functions and are to be read and executed by the processing circuitry 240. Further, the image storage circuitry 220 is configured to store therein various types of image data. For example, the image storage circuitry 220 is configured to store therein the medical image data acquired from the medical image diagnosis apparatus 10. Further, for example, the image storage circuitry 220 is configured to store therein the relevant image data acquired from the medical information processing apparatus 30. Further, for example, the image storage circuitry 220 is configured to store therein the medical image data resulting from the image processing processes and acquired from the medical information processing apparatus 40. Further, the model storage circuitry 230 is configured to store therein a trained model provided with a function to specify relevant image data and an image processing process, on the basis of input information including medical image data and medical examination information. The image data stored in the image storage circuitry 220 and the trained model stored in the model storage circuitry 230 will be explained later.

The storage circuitry 210, the image storage circuitry 220, and the model storage circuitry 230 are each realized, for example, by using a semiconductor memory element such as a Random Access Memory (RAM), a flash memory, or the like, or a hard disk, an optical disk, or the like. Further, the image storage circuitry 220 is an example of an image storage unit or the image memory. Further, the model storage circuitry 230 is an example of a model storage unit or a memory.

The processing circuitry 240 is configured to control operations of the entirety of the medical information processing apparatus 20, by executing an acquiring function 241, an evaluating function 242, a specifying function 243, a model generating function 244, a controlling function 245, and an output function 246. The acquiring function 241 is an example of an acquiring unit. The evaluating function 242 is an example of an evaluating unit. The specifying function 243 is an example of a specifying unit. The model generating function 244 is an example of a model generating unit. The controlling function 245 is an example of a controlling unit.

For example, the processing circuitry 240 is configured to acquire the medical image data from the medical image diagnosis apparatus 10 by reading and executing a program corresponding to the acquiring function 241 from the storage circuitry 210. Further, the acquiring function 241 is configured to acquire the relevant image data from the medical information processing apparatus 30. Further, the acquiring function 241 is configured to acquire the medical image data resulting from the image processing processes, from the medical information processing apparatus 40. Further, for example, the processing circuitry 240 is configured to give an evaluation to the relevant image data and the image processing process specified by the trained model on the basis of the input information, by reading and executing a program corresponding to the evaluating function 242 from the storage circuitry 210. Further, for example, the processing circuitry 240 is configured to specify the input information and the evaluation as learning data, by reading and executing a program corresponding to the specifying function 243 from the storage circuitry 210. Further, for example, the processing circuitry 240 is configured to generate the trained model on the basis of learning data and to store the generated trained model into the model storage circuitry 230, by reading and executing a program corresponding to the model generating function 244 from the storage circuitry 210. Further, for example, the processing circuitry 240 is configured to cause the trained model to specify the relevant image data and the image processing process on the basis of the input information including the medical image data and the medical examination information, by reading and executing a program corresponding to the controlling function 245 from the storage circuitry 210. Further, for example, the processing circuitry 240 is configured to output, to the terminal device 50, such a piece of image data from among the pieces of image data stored in the image storage circuitry 220 that corresponds to the request from the terminal device 50, by reading and executing a program corresponding to the output function 246 from the storage circuitry 210. Processes performed by the processing circuitry 240 will be explained later.

In the medical information processing apparatus 20 illustrated in FIG. 2, the processing functions are stored in the storage circuitry 210 in the form of computer-executable programs. The processing circuitry 240 is a processor configured to realize the functions corresponding to the programs, by reading and executing programs from the storage circuitry 210. In other words, the processing circuitry 240 that has read the programs has the functions corresponding to the read programs.

With reference to FIG. 2, the example was explained in which the single processing circuit (i.e., the processing circuitry 240) realizes the acquiring function 241, the evaluating function 242, the specifying function 243, the model generating function 244, the controlling function 245, and the output function 246; however, another arrangement is also acceptable in which the processing circuitry 240 is structured by combining together a plurality of independent processors, so that the processing functions are realized as a result of the processors executing the programs. Further, the processing functions of the processing circuitry 240 may be realized as being distributed among or integrated into one or more processing circuits, as appropriate.

Next, a configuration of the medical information processing apparatus 40 will be explained, with reference to FIG. 3. FIG. 3 is a block diagram illustrating an exemplary configuration of the medical information processing apparatus 40 according to the first embodiment. For example, as illustrated in FIG. 3, the medical information processing apparatus 40 includes an input interface 410, a display 420, storage circuitry 430, image storage circuitry 440, and processing circuitry 450.

The input interface 410 is configured to receive various types of input operations from an operator, to convert the received input operations into electric signals, and to output the electric signals to the processing circuitry 450. For example, the input interface 410 is realized by using a mouse, a keyboard, a trackball, a switch, a button, a joystick, a touchpad on which an input operation is performed by touching the operation surface thereof, a touch screen in which a display screen and a touchpad are integrally formed, a contactless input circuit using an optical sensor, an audio input circuit, and/or the like. The input interface 410 may be configured by using a tablet terminal or the like capable of wirelessly communicating with the main body of the medical information processing apparatus 40. Further, the input interface 410 does not necessarily have to include one or more physical operation component parts such as a mouse and a keyboard. For instance, possible examples of the input interface 410 include an electric signal processing circuit configured to receive an electric signal corresponding to an input operation from an external input device provided separately from the medical information processing apparatus 40 and to output the electric signal to the processing circuitry 450.

The display 420 is configured to display various types of information. For example, under control of the processing circuitry 450, the display 420 is configured to display any of medical images acquired from the medical information processing apparatus 20 and any of medical images resulting from image processing processes performed by an image processing function 452. Further, the display 420 is configured to display a Graphical User Interface (GUI) used for receiving various types of instructions and various types of settings from the operator via the input interface 410. For example, the display 420 may be a liquid crystal display monitor or a Cathode Ray Tube (CRT) display monitor. The display 420 may be of a desktop type or may be configured by using a table terminal or the like capable of wirelessly communicating with the main body of the medical information processing apparatus 40.

The storage circuitry 430 is configured to store therein programs that correspond to various types of functions and are to be read and executed by the processing circuitry 450. Further, the image storage circuitry 440 is configured to store therein various types of image data. For example, the image storage circuitry 440 is configured to store therein the medical image data acquired from the medical information processing apparatus 20. Further, for example, the image storage circuitry 440 is configured to store therein the medical image data resulting from the image processing processes performed by the image processing function 452. The storage circuitry 430 and the image storage circuitry 440 are each realized by using, for example, a semiconductor memory element such as a RAM, a flash memory, or the like, or a hard disk, an optical disk, or the like.

The processing circuitry 450 is configured to control operations of the entirety of the medical information processing apparatus 40, by executing an acquiring function 451, the image processing function 452, a display controlling function 453, and an output function 454. For example, the processing circuitry 450 is configured to acquire the medical image data from the medical information processing apparatus 20, by reading and executing a program corresponding to the acquiring function 451 from the storage circuitry 430. Further, for example, the processing circuitry 450 is configured to perform the image processing processes on the basis of the medical image data acquired from the medical information processing apparatus 20, by reading and executing a program corresponding to the image processing function 452 from the storage circuitry 430. Further, for example, the processing circuitry 450 is configured to cause the display 420 to display any of the medical image data acquired from the medical information processing apparatus 20 and any of the medical image data resulting from the image processing processes performed by the image processing function 452, by reading and executing a program corresponding to the display controlling function 453 from the storage circuitry 430. Further, for example, the processing circuitry 450 is configured to output the medical image data resulting from the image processing processes performed by the image processing function 452 to the medical information processing apparatus 20, by reading and executing a program corresponding to the output function 454 from the storage circuitry 430. Processes performed by the processing circuitry 450 will be explained later.

In the medical information processing apparatus 40 illustrated in FIG. 3, the processing functions are stored in the storage circuitry 430 in the form of computer-executable programs. The processing circuitry 450 is a processor configured to realize the functions corresponding to the programs, by reading and executing the programs from the storage circuitry 430. In other words, the processing circuitry 450 that has read the programs has the functions corresponding to the read programs.

With reference to FIG. 3, the example was explained in which the single processing circuit (i.e., the processing circuitry 450) realizes the acquiring function 451, the image processing function 452, the display controlling function 453, and the output function 454; however, another arrangement is also acceptable in which the processing circuitry 450 is structured by combining together a plurality of independent processors, so that the processing functions are realized as a result of the processors executing the programs. Further, the processing functions of the processing circuitry 450 may be realized as being distributed among or integrated together into one or more processing circuits, as appropriate.

Figure 4:
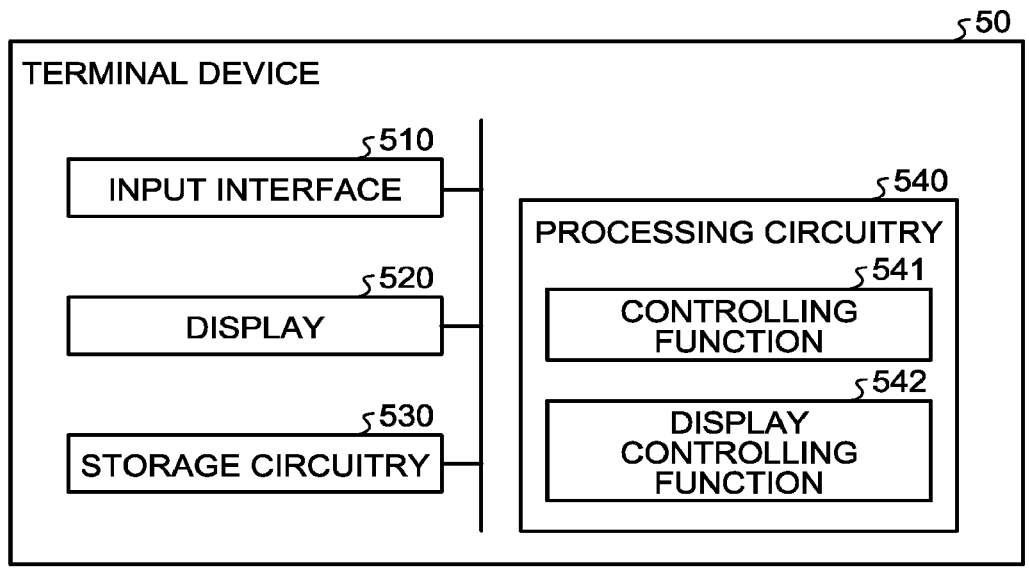
FIG. 4 is a block diagram illustrating an exemplary configuration of a terminal device according to the first embodiment.

Next, a configuration of the terminal device 50 will be explained, with reference to FIG. 4. FIG. 4 is a block diagram illustrating an exemplary configuration of the terminal device 50 according to the first embodiment. For example, as illustrated in FIG. 4, the terminal device 50 includes an input interface 510, a display 520, storage circuitry 530, and processing circuitry 540.

The input interface 510 is configured to receive various types of input operations from an operator, to convert the received input operations into electric signals, and to output the electric signals to the processing circuitry 540. For example, the input interface 510 is realized by using a mouse, a keyboard, a trackball, a switch, a button, a joystick, a touchpad on which an input operation is performed by touching the operation surface thereof, a touch screen in which a display screen and a touchpad are integrally formed, a contactless input circuit using an optical sensor, an audio input circuit, and/or the like.

The display 520 is configured to display various types of information. For example, under control of the processing circuitry 540, the display 520 is configured to display any of the various types of images stored in the image storage circuitry 220 of the medical information processing apparatus 20. Further, the display 520 is configured to display a GUI used for receiving various types of instructions and various types of settings from the operator via the input interface 410. For example, the display 520 may be a liquid crystal display monitor or a CRT display monitor.

The storage circuitry 530 is configured to store therein programs that correspond to various types of functions and are to be read and executed by the processing circuitry 540. The storage circuitry 530 is realized by using, for example, a semiconductor memory element such as a RAM, a flash memory, or the like, or a hard disk, an optical disk, or the like.

The processing circuitry 540 is configured to control operations of the entirety of the terminal device 50 by executing a controlling function 541 and a display controlling function 542. For example, the processing circuitry 540 is configured to control the operations of the entirety of the terminal device 50 on the basis of input operations received from the operator via the input interface 510, by reading and executing a program corresponding to the controlling function 541 from the storage circuitry 530. Further, for example, the processing circuitry 540 is configured to cause the display 520 to display any of the medical image data stored in the image storage circuitry 220 of the medical information processing apparatus 20, by reading and executing a program corresponding to the display controlling function 542 from the storage circuitry 530. Further, the display controlling function 542 is configured to cause the display 520 to display any of the relevant image data stored in the image storage circuitry 220 and any of the medical image data resulting from the image processing processes performed by the image processing function 452. The image data caused to be displayed by the display controlling function 542 will be explained later.

In the terminal device 50 illustrated in FIG. 4, the processing functions are stored in the storage circuitry 530 in the form of computer-executable programs. The processing circuitry 540 is a processor configured to realize the functions corresponding to the programs, by reading and executing the programs from the storage circuitry 530. In other words, the processing circuitry 540 that has read the programs has the functions corresponding to the read programs.

With reference to FIG. 4, the example was explained in which the single processing circuit (i.e., the processing circuitry 540) realizes the controlling function 541 and the display controlling function 542; however, another arrangement is also acceptable in which the processing circuitry 540 is structured by combining together a plurality of independent processors, so that the processing functions are realized as a result of the processors executing the programs. Further, the processing functions of the processing circuitry 540 may be realized as being distributed among or integrated into one or more processing circuits, as appropriate.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). Each of the processors realizes the functions by reading and executing the programs saved in the storage circuitry 210, the storage circuitry 430, or the storage circuitry 530.

FIGS. 2, 3, and 4 illustrate the examples in which the single storage circuit (the storage circuitry 210, the storage circuitry 430, or the storage circuitry 530) stores therein the programs corresponding to the processing functions. However, it is also acceptable to provide a plurality of storage circuitry 210 in a distributed manner, so that the processing circuitry 240 reads a corresponding program from each of the individual storage circuitry 210. Similarly, it is also acceptable to provide a plurality of storage circuitry 430 in a distributed manner, so that the processing circuitry 450 reads a corresponding program from each of the individual storage circuitry 430. Similarly, it is also acceptable to provide a plurality of storage circuitry 530 in a distributed manner, so that the processing circuitry 540 reads a corresponding program from each of the individual storage circuitry 530. Furthermore, instead of saving the programs in the storage circuitry 210, the storage circuitry 430, or the storage circuitry 530, it is also acceptable to directly incorporate the programs into the circuitry of one or more processors. In that situation, the one or more processors realize the functions by reading and executing the programs incorporated in the circuitry thereof.

Further, the processing circuitry 240, the processing circuitry 450, and the processing circuitry 540 may each be configured to realize the functions thereof by using a processor of an external device connected via the network NW. For example, the processing circuitry 240 may be configured to realize the functions illustrated in FIG. 2, by reading and executing the programs corresponding to the functions from the storage circuitry 210 and by using a group of servers (a cloud) connected to the medical information processing apparatus 20 via the network NW as computational resources.

The exemplary configuration of the medical information processing system 1 has thus been explained. The medical information processing apparatus 20 included in the medical information processing system 1 structured as described above is configured to improve a workflow from the acquisition to the interpretation of the medical image data.

Figure 5:
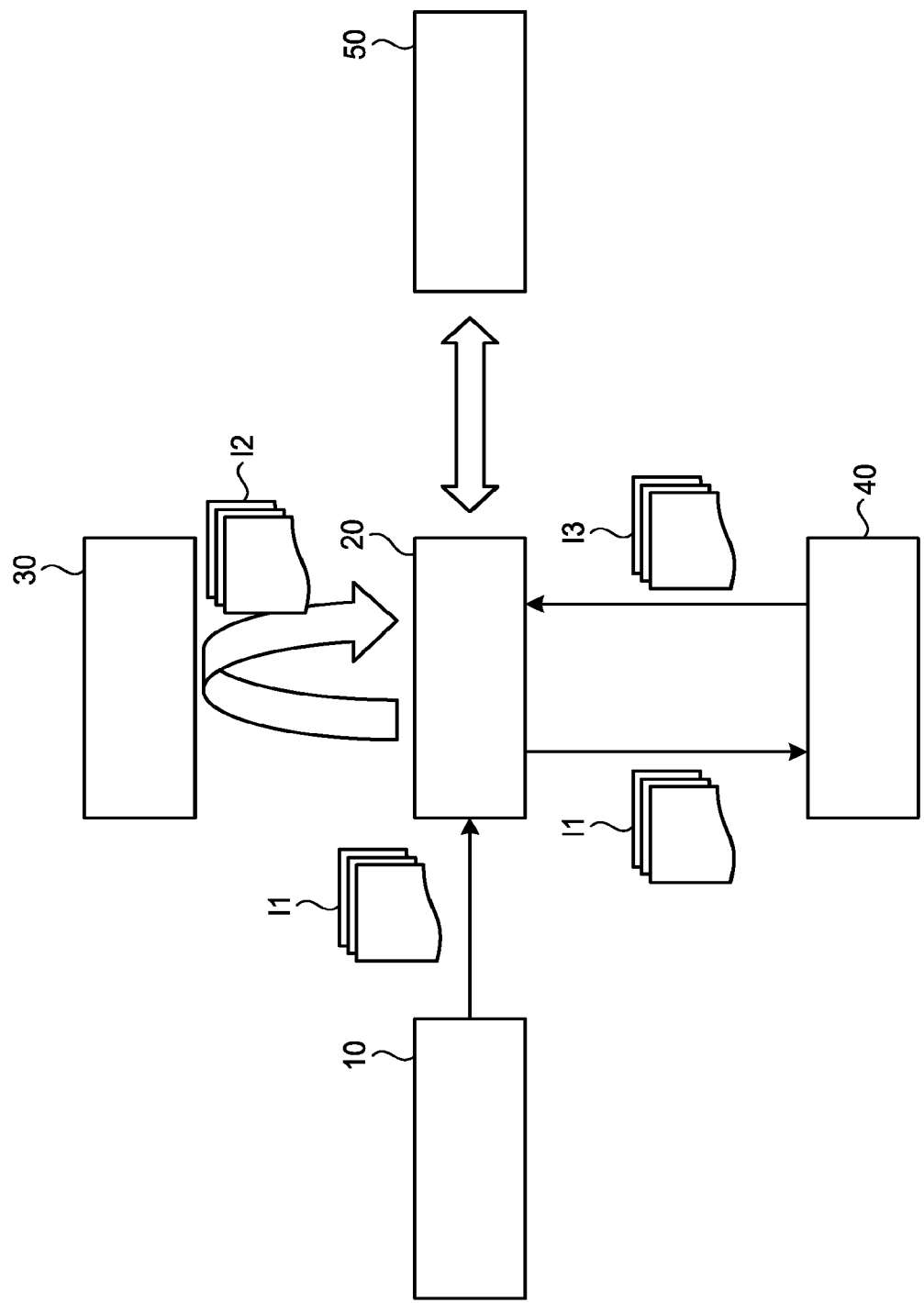
FIG. 5 is a drawing illustrating an example of a workflow according to the first embodiment.

Next, the workflow from the acquisition to the interpretation of the medical image data will be explained with reference to FIG. 5. FIG. 5 is a drawing illustrating an example of a workflow according to the first embodiment. In the example in FIG. 5, at first, the medical image diagnosis apparatus 10 acquires medical image data I1 from a patient. Subsequently, the acquiring function 241 of the medical information processing apparatus 20 acquires the medical image data I1 from the medical image diagnosis apparatus 10. For example, the acquiring function 241 receives the medical image data I1 output from the medical image diagnosis apparatus 10 and stores the received data into the image storage circuitry 220.

After that, the acquiring function 241 of the medical information processing apparatus 20 acquires relevant image data I2 relevant to the medical image data I1 from the medical information processing apparatus 30. In this situation, the relevant image data I2 may be, for example, an image of the same patient as the patient imaged in the medical image data I1 or an image of a patient having a clinical case that is the same as or similar to that of the patient imaged in the medical image data I1.

In one example, when the medical image data I1 is an image acquired from a patient P1, the relevant image data I2 may be an image acquired of the patient P1 in the past. In another example, when the medical image data I1 is an image acquired from the patient P1, the relevant image data I2 may be an image acquired from a patient P2 having a clinical case that is the same as or similar to that of the patient P1. The medical image data I1 and the relevant image data I2 may be pieces of image data of mutually-different types. For example, when the medical image data I1 is CT image data, the relevant image data I2 may be ultrasound image data.

For example, the acquiring function 241 is configured to acquire the relevant image data I2 in response to an input operation performed by an operator (e.g., a medical technologist) of the medical information processing apparatus 20. More specifically, the operator searches for images of the same patient as the patient imaged in the medical image data I1 and images of one or more other patients having a clinical case that is the same as or a similar to that of the patient imaged the medical image data I1 or the like and further selects one or more images that may be used as a reference in the interpretation of the medical image data I1. Further, the acquiring function 241 acquires the selected images as the relevant image data I2 and stores the acquired relevant image data I2 into the image storage circuitry 220.

Further, the output function 246 is configured to output the medical image data I1 to the medical information processing apparatus 40. In this situation, the acquiring function 451 of the medical information processing apparatus 40 is configured to receive the medical image data I1 output by the output function 246 and to store the received data into the image storage circuitry 440. In other words, the acquiring function 451 is configured to acquire the medical image data I1 from the medical information processing apparatus 20. Subsequently, the image processing function 452 is configured to perform an image processing process on the basis of the medical image data I1. In the following sections, the image processing process performed on the basis of the medical image data I1 will be referred to as an image processing process A1.

For example, the image processing function 452 is configured to perform the image processing process A1 in response to an input operation performed by the operator (e.g., a medical technologist) of the medical information processing apparatus 40. More specifically, the operator selects the type and parameters of the image processing process A1 so as to generate an image that can be used as a reference in the interpretation of the medical image data I1. Further, on the basis of the medical image data I1, the image processing function 452 performs the image processing process A1 corresponding to the selected type and parameters.

In one example, as the image processing process A1, the image processing function 452 performs a process of generating three-dimensional image data on the basis of the medical image data I1 that is two-dimensional and further generating two-dimensional image data on the basis of the three-dimensional image data. In the following sections, an example will be explained in which the medical image data I1 is CT image data (a plurality of tomographic images). First, the acquiring function 451 acquires the plurality of tomographic images from the medical information processing apparatus 20. Subsequently, the image processing function 452 generates three-dimensional image data on the basis of the plurality of tomographic images. For example, the image processing function 452 generates the three-dimensional image data by arranging the plurality of tomographic images in a three-dimensional space and performing an interpolation process among the tomographic images. Subsequently, the image processing function 452 generates the two-dimensional image data by performing any of various types of rendering processes on the generated three-dimensional data. An example of the rendering processes is a process of reconstructing two-dimensional image data on an arbitrary cross-sectional plane from the three-dimensional image data by implementing a Multi Planar Reconstruction (MPR) method. Other examples of the rendering processes include a volume rendering process and a process of generating two-dimensional image data reflecting three-dimensional information from the three-dimensional image data by implementing a Maximum Intensity Projection (MIP) method.

For example, the image processing function 452 is configured to generate various types of two-dimensional image data from the three-dimensional image data in response to an input operation performed by the operator (e.g., the medical technologist) of the medical information processing apparatus 40. Further, the display controlling function 453 is configured to cause the display 420 to display the generated two-dimensional image data. In this situation, the operator references the various types of two-dimensional image data and selects interpretation-purpose two-dimensional image data. For example, from among pieces of two-dimensional image data taken on various cross-sectional planes, the operator selects a piece of two-dimensional image data rendering an examined site or a lesion particularly clearly, as the interpretation-purpose two-dimensional image data.

In this regard, the interpretation-purpose two-dimensional image data based on the three-dimensional image data may be referred to as a Secondary Capture (SC) image. Although it may be impossible to display three-dimensional image data on certain apparatuses in some situations, SC images are usually displayable on any arbitrary apparatus. In other words, although it is impossible to display three-dimensional image data on such apparatuses that do not have an application for displaying three-dimensional images, it is usually possible to display SC images, which are represented by two-dimensional image data, on any arbitrary apparatus.

In another example, the image processing function 452 may be configured to generate a fusion image, as the three-dimensional image data based on the medical image data I1. For example, at first, the medical image diagnosis apparatus 10 acquires CT image data corresponding to a plurality of phases, as the medical image data I1. In one example, the medical image diagnosis apparatus 10 acquires CT image data acquired by injecting a contrast agent into a blood vessel of the patient including a piece of CT image data (hereinafter, "first CT image data") taken at the time when the concentration of the contrast agent in an artery is at a maximum and another piece of CT image data (hereinafter "second CT image data") taken at the time when the concentration of the contrast agent in a vein is at a maximum.

In this situation, as the medical image data I1, the acquiring function 241 acquires the first CT image data and the second CT image data from the medical image diagnosis apparatus 10. Subsequently, the acquiring function 451 acquires the first CT image data and the second CT image data from the medical information processing apparatus 20. After that, on the basis of the first CT image data and the second CT image data, the image processing function 452 generates the fusion image.

More specifically, the image processing function 452 generates three-dimensional image data (hereinafter, "artery phase image") based on the first CT image data and three-dimensional image data (hereinafter, "vein phase image") based on the second CT image data. Subsequently, the image processing function 452 generates the fusion image by combining together the artery phase image and the vein phase image. After that, the image processing function 452 generates the two-dimensional image data by performing any of the various types of rendering processes on the generated fusion image and further receives an operation to select interpretation-purpose two-dimensional image data from the operator. In other words, the image processing function 452 generates an SC image based on the fusion image.

In yet another example, as the image processing process A1, the image processing function 452 may be configured to perform an analyzing process based on the medical image data I1. For example, the image processing function 452 analyzes a lesion on the basis of the medical image data I1. In one example, on the basis of the medical image data I1, the image processing function 452 detects the position of lesion and/or measures the volume, the area, the length, and the like of the detected lesion.

Further, for example, as the analyzing process based on the medical image data I1, the image processing function 452 may perform a perfusion analysis. In one example, the medical image diagnosis apparatus 10 acquires, as the medical image data I1, a plurality of pieces of SPECT image data taken of the heart of the patient at time intervals. Subsequently, the acquiring function 241 acquires the plurality of pieces of SPECT image data from the medical image diagnosis apparatus 10. After that, the acquiring function 451 acquires the plurality of pieces of SPECT image data from the medical information processing apparatus 20. Subsequently, on the basis of a comparison among the plurality of pieces of SPECT image data, the image processing function 452 obtains hemodynamics of blood vessels in the heart of the patient. For example, because accumulation of a radioactive drug is slower in ischemic regions, the image processing function 452 identifies positions where pixel values change by smaller amounts as an ischemic region, by comparing the plurality of pieces of SPECT image data with one another.

Further, the image processing function 452 is configured to generate an image indicating a result of the analyzing process. For example, the image processing function 452 generates an image in which a marker is appended to the position of the lesion detected from the medical image data I1. Further, for example, the image processing function 452 generates an image in which a marker is appended to the ischemic region identified in the medical image data I1.

Subsequently, the acquiring function 241 of the medical information processing apparatus 20 acquires the medical image data I1 resulting from the image processing process A1, from the medical information processing apparatus 40. In the following sections, the medical image data I1 resulting from the image processing process A1 will be referred to as medical image data I3. In other words, as illustrated in FIG. 5, the acquiring function 241 acquires the medical image data I3 from the medical information processing apparatus 40. The medical image data I3 may be, for example, an SC image, an image indicating a result of the analyzing process, and the like. Further, the acquiring function 241 stores the acquired medical image data I3 into the image storage circuitry 220.

Figure 6:
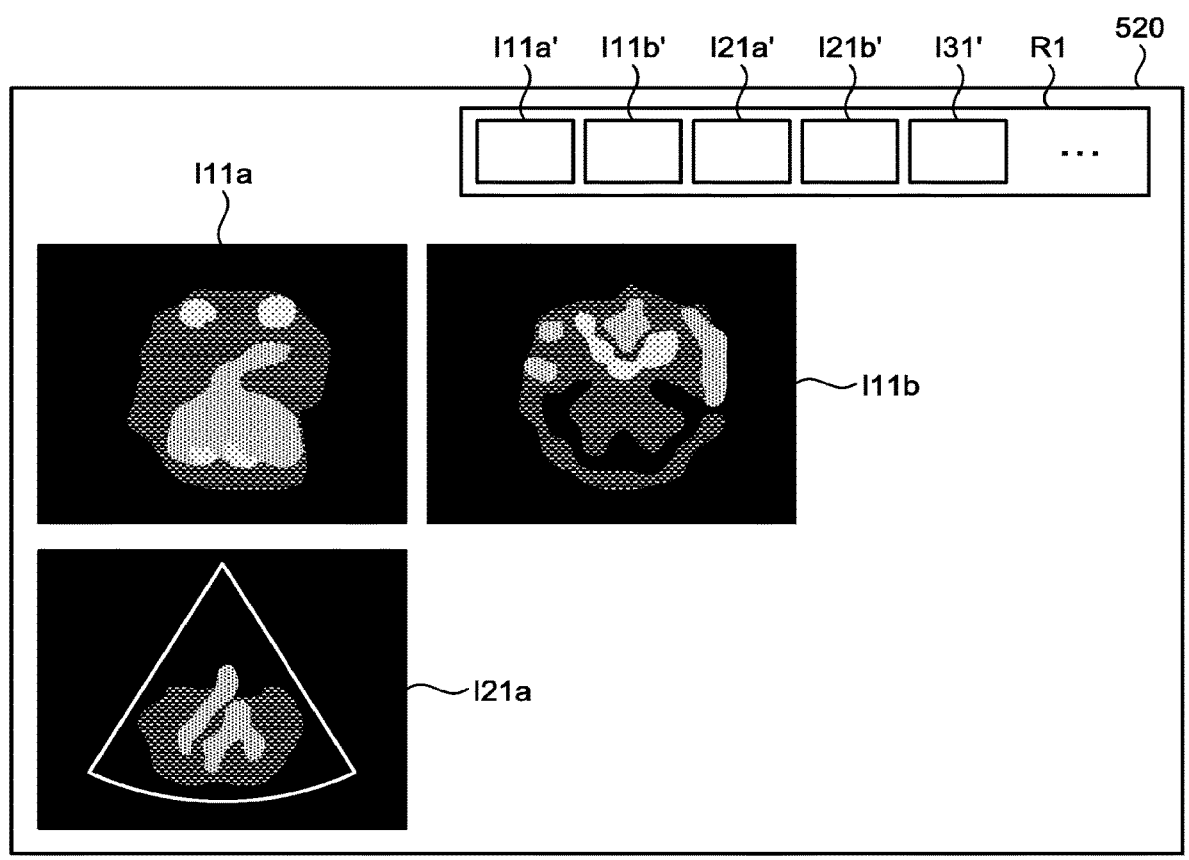
FIG. 6 is a drawing illustrating an example of display of images according to the first embodiment.

In this situation, from among the pieces of image data (the medical image data I1, the relevant image data I2, the medical image data I3, and the like) stored in the image storage circuitry 220, the output function 246 of the medical information processing apparatus 20 outputs the image data corresponding to a request from the terminal device 50, to the terminal device 50. This process will be explained below, with reference to FIG. 6. FIG. 6 illustrates, as examples of the medical image data I1, medical image data I11a and medical image data I11b. Also, with reference to FIG. 6, as examples of the relevant image data I2, relevant image data I21a and relevant image data I21b will be explained. Further, with reference to FIG. 6, as an example of the medical image data I3, medical image data I31 will be explained. FIG. 6 is a drawing illustrating an example of display of the images according to the first embodiment.

At first, the display controlling function 542 of the terminal device 50 causes the display 520 to display, in a region R1, thumbnails based on pieces of image data stored in the image storage circuitry 220. For example, as illustrated in FIG. 6, the display controlling function 542 causes the display 520 to display: a thumbnail image I11a' based on the medical image data I11a; a thumbnail image I11b' based on the medical image data I11b; a thumbnail image I21a' based on the relevant image data I21a; a thumbnail image I21b' based on the relevant image data I21b; and a thumbnail image I31' based on the medical image data I31.

Subsequently, the operator (an image interpreting doctor) of the terminal device 50 references the display of the thumbnails and selects images to be used for image interpretation. For example, as the images to be used for the image interpretation, the image interpreting doctor selects the medical image data I11a, the medical image data I11b, and the relevant image data I21a. In this situation, the display controlling function 542 acquires the medical image data I11a, the medical image data I11b, and the relevant image data I21a from the image storage circuitry 220 of the medical information processing apparatus 20 and causes the display 520 to display these pieces of image data.

More specifically, the display controlling function 542 requests the medical image data I11a, the medical image data I11b, and the relevant image data I21a from the medical information processing apparatus 20. Subsequently, the output function 246 of the medical information processing apparatus 20 reads the pieces of image data corresponding to the request (i.e., the medical image data I11a, the medical image data I11b, and the relevant image data I21a) from the image storage circuitry 220 and outputs the read pieces of image data to the terminal device 50.

After that, as illustrated in FIG. 5, the display controlling function 542 causes the medical image data I11a, the medical image data I11b, and the relevant image data I21a to be displayed. The medical image data I11a and the medical image data I11b illustrated in FIG. 5 are each CT image data. The relevant image data I21a is ultrasound image data. The image interpreting doctor interprets the medical image data I11a and the medical image data I11b, while referencing the relevant image data I21a, to prepare an observation report.

As explained above, by using the medical information processing apparatus 20, it is possible to provide the image interpreting doctor with the relevant image data I2 and the medical image data I3, in addition to the medical image data I1. With this arrangement, the image interpreting doctor is able to prepare the observation report more properly compared to the situation where only the medical image data I1 is used. However, as explained above, the acquisition of the relevant image data I2 and the image processing process A1 are performed on the basis of the input operations performed by the operators of the medical information processing apparatus 20 and the medical information processing apparatus 40. Accordingly, a workflow from the acquisition to the interpretation of the medical image data I1 can be complicated.

To cope with this situation, there may be an idea suggesting that the workflow from the acquisition to the interpretation of the medical image data I1 be automated based on rules. For example, it may be possible to automate a part of the workflow from the acquisition to the interpretation of the medical image data I1, by setting a rule in advance such as "images of the same patient from the last three years are acquired as the relevant image data I2". However, because it would be necessary to create such a rule for each of various patterns corresponding to clinical cases, patient information, types of image data, and the like, it would not be easy to create the rules. Further, it would also be necessary to review the created rules as appropriate. For example, it would be necessary to review the rules every time when a new medical image diagnosis apparatus 10 is introduced, when a medical examination protocol is changed, and/or when the number of image processing processes executable by the medical information processing apparatus 40 has increased due to development of a new clinical application.

Further, when there is insufficiency in one or both of the acquisition of the relevant image data I2 and the image processing process A1 based on the medical image data I1, it would be necessary to perform the one or both of the acquisition of the relevant image data I2 and the image processing process A1 again, which would be a burden for the image interpreting doctor and the medical technologist. Further, when one or both of the acquisition of the relevant image data I2 and the image processing process based on the medical image data I1 are performed excessively, there is a possibility that a waiting time period might be incurred because it would take a longer period of time to perform the acquisition of the relevant image data I2 and the image processing process A1.

To cope with the circumstances described above, the medical information processing apparatus 20 is configured to improve the workflow from the acquisition to the interpretation of the medical image data I1, by using a trained model provided with a function to specify a relevant image data and an image processing process. The following will describe processes performed by the medical information processing apparatus 20 to generate the trained model and to improve the workflow by using the trained model.

At first, the model generating function 244 is configured to generate a trained model M1 and to store the generated trained model M1 into the model storage circuitry 230. For example, the model generating function 244 generates the trained model M1 through supervised learning based on a workflow carried out in the past.

More specifically, the model generating function 244 at first obtains medical image data I12 acquired by the acquiring function 241 from the medical image diagnosis apparatus 10 and medical examination information T12 related to the medical image data I12, in the workflow carried out in the past. The medical image data I12 is an example of the medical image data I1. Further, the medical examination information T12 is an example of the medical examination information T1 related to medical image data I1.

In this situation, the medical examination information T12 may be, for example, order information used at the time of acquiring the medical image data I12. In other words, the medical image diagnosis apparatus 10 acquires the medical image data I12 by performing an image taking process according to the order information. The order information contains, for example, patient information (the patient's ID, name, gender, and date of birth, etc.), the requesting department, the requesting medical doctor, an emergency category, the date and time of the image taking process, the name of the modality, the image taking method, the examined site, and the like. For example, by connecting to an electronic medical record system via the network NW, the model generating function 244 is able to obtain the order information used at the time of acquiring the medical image data I12.

In another example, the medical examination information T12 may be additional information to the medical image data I12. For example, when the medical image data I12 is data in a Digital Imaging and Communications in Medicine (DICOM) format, a DICOM tag of the medical image data I12 has recorded therein additional information such as patient information, the requesting department, the requesting medical doctor, the date and time of the image taking process, the name of the modality, the image taking method, the examined site, and the like. By referring to the DICOM tag, the model generating function 244 is able to obtain the additional information to the medical image data I12.

Further, the model generating function 244 is configured to obtain relevant image data I2 (hereinafter, "relevant image data I22") that is relevant to the medical image data I12 and was acquired in response to an input operation performed by the operator of the medical information processing apparatus 20. In other words, the model generating function 244 obtains the relevant image data I22 selected by the operator. Further, the model generating function 244 is configured to obtain an image processing process A1 (hereinafter "image processing process A12") performed in response to an input operation from the operator of the medical information processing apparatus 40. In other words, the model generating function 244 obtains the type and parameters of the image processing process A12 selected by the operator.

Subsequently, the model generating function 244 generates the trained model M1 through supervised learning while using the medical image data I12, the medical examination information T12, the relevant image data I22, and the image processing process A12 as learning data. More specifically, the model generating function 244 inputs, to a machine learning engine, the medical image data I12 and the medical examination information T12 as input-side data, and the relevant image data I22 and the image processing process A12 as output-side data. Subsequently, the machine learning engine learns a relationship between the input-side data and the output-side data. For example, the machine learning engine learns the relationship between the input-side data and the output-side data, by using any of various types of algorithms such as deep learning, a neural network, a logistic regression analysis, a non-linear discriminant analysis, a Support Vector Machine (SVM), a random forest, a Naïve Bayes scheme, and the like. Further, the model generating function 244 is configured to store the generated trained model M1 into the model storage circuitry 230.

As the input-side data, it is also possible to use any other various types of information, besides the medical image data I12 and the medical examination information T12. For example, besides the medical image data I12 and the medical examination information T12, the model generating function 244 may use, as the input-side data, information about the image interpreting doctor, as well as information about the medical technologist who selected the relevant image data I22 and about the medical technologist who selected the image processing process A12, or the like. In other words, the model generating function 244 generates the trained model M1 through the supervised learning while using, as learning data, input information including the medical image data I12 and the medical examination information T12, as well as the relevant image data I22 and the image processing process A12. As a result, the trained model M1 is provided with a function to specify the relevant image data I2 and the image processing process A1 on the basis of the input information including the medical image data I1 and the medical examination information T1.

Further, although the example was explained in which the model generating function 244 generates the trained model M1, the trained model M1 may be generated by an apparatus other than then medical information processing apparatus 20. In that situation, the model generating function 244 obtains the trained model M1 via the network NW and stores the obtained trained model M1 into the model storage circuitry 230.

When the medical image diagnosis apparatus 10 has further acquired medical image data I13 after the trained model M1 is stored in the model storage circuitry 230, the acquiring function 241 acquires the medical image data I13 from the medical image diagnosis apparatus 10 and stores the acquired data into the image storage circuitry 220. In this situation, the controlling function 245 reads the trained model M1 from the model storage circuitry 230 and causes the trained model M1 to specify relevant image data (hereinafter "relevant image data I23") relevant to the medical image data I13 and an image processing process (hereinafter, "image processing process A13") performed based on the medical image data I13. In this situation, the medical image data I13 is an example of the medical image data I1. Further, the relevant image data I23 is an example of the relevant image data I2. Also, the image processing process A13 is an example of the image processing process A1.

Figure 7:
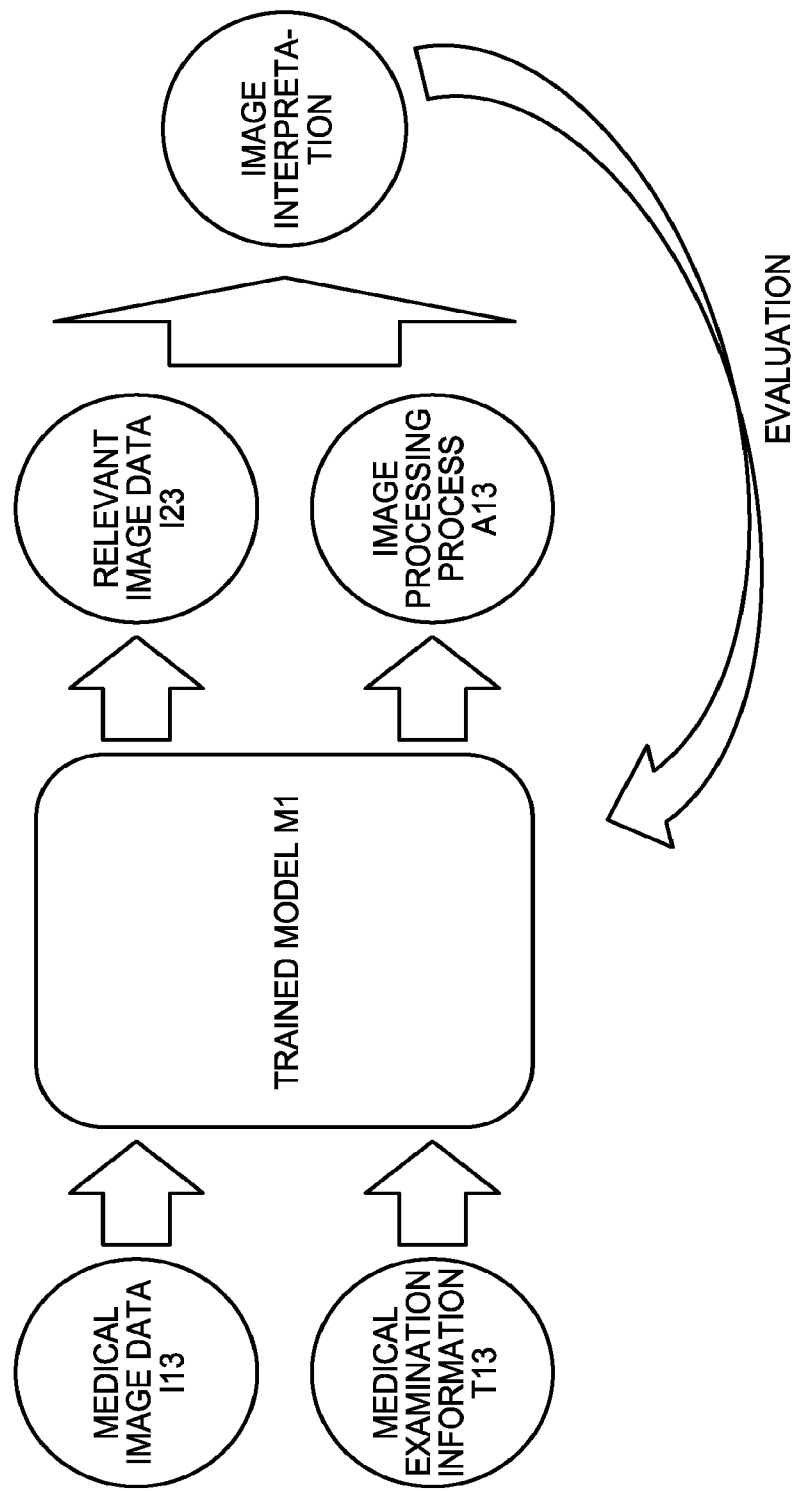
FIG. 7 is a drawing for explaining a trained model according to the first embodiment.

More specifically, as illustrated in FIG. 7, the controlling function 245 inputs the medical image data I13 and medical examination information T13 related to the medical image data I13 to the trained model M1. In this situation, the controlling function 245 may input other various types of information besides the medical image data I13 and the medical examination information T13, to the trained model M1. In other words, the controlling function 245 inputs input information including the medical image data I13 and the medical examination information T13 to the trained model M1. Accordingly, the controlling function 245 causes the trained model M1 to specify the relevant image data I23 and the image processing process A13. FIG. 7 is a drawing for explaining the trained model according to the first embodiment.

Subsequently, the acquiring function 241 acquires the relevant image data I23 specified by the trained model M1 from the medical information processing apparatus 30 and stores the acquired data into the image storage circuitry 220. Further, the output function 246 outputs the medical image data I13 to the medical information processing apparatus 40. After that, the image processing function 452 of the medical information processing apparatus 40 performs the image processing process A13 specified by the trained model M1, on the basis of the medical image data I13. Subsequently, the acquiring function 241 acquires medical image data I13 (hereinafter "medical image data I33") resulting from the image processing process A13 from the medical information processing apparatus 40 and stores the acquired data into the image storage circuitry 220. In this situation, the medical image data I33 is an example of the medical image data I3.

After that, the display controlling function 542 of the terminal device 50 causes the display 520 to display the medical image data I13 acquired by the acquiring function 241. Further, the display controlling function 542 causes the display 520 to display the relevant image data I23 and the medical image data I33 acquired by the acquiring function 241. More specifically, in response to an input operation performed by the image interpreting doctor, the display controlling function 542 requests the image data from the medical information processing apparatus 20. Subsequently, from among the pieces of image data (the medical image data I13, the relevant image data I23, the medical image data I33, and the like) stored in the image storage circuitry 220, the output function 246 outputs the image data corresponding to the request, to the terminal device 50. After that, the display controlling function 542 receives the image data output by the output function 246 and causes the display 520 to display the output image data. Further, the image interpreting doctor interprets the medical image data I13 while referencing the relevant image data I23 and the medical image data I33 to prepare an observation report.

As explained above, the medical information processing apparatus 20 is configured to specify the relevant image data I23 and the image processing process A13 by using the trained model M1. In other words, by using the medical information processing apparatus 20, it is possible to simplify the workflow from the acquisition to the interpretation of the medical image data I13, by automating the acquisition of the relevant image data I23 and the image processing process A13 based on the medical image data I13.

Subsequently, the evaluating function 242 is configured to give an evaluation to the relevant image data I23 and the image processing process A13 specified by the trained model M1. More specifically, the evaluating function 242 gives the evaluation indicating how appropriate the relevant image data I23 and the image processing process A13 specified by the trained model M1 were, for the interpretation of the medical image data I13.

Next, the evaluation given by the evaluating function 242 will be explained, with reference to FIG. 8. FIG. 8 is a table illustrating examples of the evaluation according to the first embodiment. In FIG. 8, "No Excess or Insufficiency" means that the relevant image data I23 and the medical image data I33 based on the image processing process A13 were each used for the interpretation of the medical image data I13 and that there was no other image data used besides the relevant image data I23 and the medical image data I33. Further, "Excess" means that, although there was no other image data used for the interpretation of the medical image data I13 besides the relevant image data I23 and the medical image data I33, there was certain image data that was not used from among the relevant image data I23 and the medical image data I33. Further, "Delay" means that a waiting time period was incurred by using the relevant image data I23 and the medical image data I33 during the interpretation of the medical image data I13. Further, "Insufficiency" means that although the relevant image data I23 and the medical image data I33 were each used, there was other image data used besides the relevant image data I23 and the medical image data I33.

With respect to the relevant image data I23 and the image processing process A13 specified by the trained model M1, the evaluating function 242 judges which one of the descriptions "No Excess or Insufficiency", "Excess", "Delay", and "Insufficiency" corresponds to the specified information and gives an evaluation corresponding to the determined result. For example, when determining that the specified information corresponds to "No Excess or Insufficiency", the evaluating function 242 gives an evaluation "+2" to the relevant image data I23 and the image processing process A13. As another example, when determining that the specified information corresponds to "Excess", the evaluating function 242 gives an evaluation "+1" to the relevant image data I23 and the image processing process A13. As yet another example, when determining that the specified information corresponds to "Delay", the evaluating function 242 gives an evaluation "−1" to the relevant image data I23 and the image processing process A13. As yet another example, when determining that the specified information corresponds to "Insufficiency", the evaluating function 242 gives an evaluation "−2" to the relevant image data I23 and the image processing process A13.

In one example, the evaluating function 242, at first, judges whether or not the relevant image data I23 and the medical image data I33 were each used for the interpretation of the medical image data I13. In this situation, it is possible to judge whether or not the relevant image data I23 and the medical image data I33 were each used, by judging whether or not the terminal device 50 displayed these pieces of data. For example, from among the relevant image data I23 and the medical image data I33, when certain piece of image data was displayed as a thumbnail in the region R1 in FIG. 5 but was not selected by the image interpreting doctor, the evaluating function 242 determines that the piece of image data was not used for the interpretation of the medical image data I13.

As another example, the evaluating function 242 may judge whether or not the relevant image data I23 and the medical image data I33 were each used, by taking into consideration the length of the time period of the display or the number of times the data has been displayed. For example, from among pieces of image data that were displayed as thumbnails in the region R1 in FIG. 5 and were selected by the image interpreting doctor, the evaluating function 242 may determine such a piece of image data that was cancelled from the selection within a predetermined threshold time period, as the data that was not used for the interpretation of the medical image data I13. In other words, the evaluating function 242 determines such a piece of image data of which the display time period is equal to or shorter than a threshold value, as the data that was not used for the interpretation of the medical image data I13. Alternatively, for example, the evaluating function 242 may determine such a piece of image data that has been displayed a number of times equal to or smaller than a threshold value, as the data that was not used for the interpretation of the medical image data I13.

As yet another example, the evaluating function 242 may judge whether or not the relevant image data I23 and the medical image data I33 were each used, by taking line-of-sight directions of the image interpreting doctor into consideration. For example, with respect to the image data that was displayed on the terminal device 50 from among the relevant image data I23 and the medical image data I33, when the line-of-sight direction of the image interpreting doctor was not directed to the display device of the terminal device 50 while the image data was being displayed, the evaluating function 242 determines that the image data was not used for the interpretation of the medical image data I13.

For example, the terminal device 50 may include a line-of-sight recognizing device and be configured to recognize a line of sight of the image interpreting doctor and to judge whether or not the line of sight of the image interpreting doctor is positioned on the display device. In this situation, the line-of-sight recognizing device may be a device including a camera or the like that images the image interpreting doctor, for example. The line-of-sight recognizing device is, for example, configured to convert the intersection point of the display screen of the display device and the line of sight into point coordinates in a two-dimensional coordinate system on the display screen and to transmit the point coordinates to the processing circuitry 240.

As yet another example, the evaluating function 242 may judge whether or not the relevant image data I23 and the medical image data I33 were each used, on the basis of a medical examination report created by the image interpreting doctor. More specifically, the evaluating function 242 determines such image data that was used in the medical examination report from among the relevant image data I23 and the medical image data I33, as data that was used for the interpretation of the medical image data I13.

From among the relevant image data I23 and the medical image data I33, when having determined that certain image data was not used for the interpretation of the medical image data I13, the evaluating function 242 determines that the relevant image data I23 and the medical image data I33 correspond to "Excess". In other words, the evaluating function 242 gives an evaluation "+1" to the relevant image data I23 and the image processing process A13, in accordance with whether or not the relevant image data I23 and the medical image data I33 were each used for the interpretation of the medical image data I13.

Further, the evaluating function 242 judges whether or not there was other image data used for the interpretation of the medical image data I13 besides the relevant image data I23 and the medical image data I33. In this situation, the image data that was used besides the relevant image data I23 and the medical image data I33 may be, for example, the relevant image data I2 acquired in response to an input operation performed by the operator of the medical information processing apparatus 20 or the medical image data I3 based on the image processing process A1 performed in response to an input operation from the operator of the medical information processing apparatus 40.

In the following sections, the relevant image data I2 that is relevant to the medical image data I13 and was acquired in response to an input operation performed by the operator of the medical information processing apparatus 20 will be referred to as relevant image data I23a. Further, in the following sections, the image processing process A1 that is based on the medical image data I13 and is performed in response to an input operation from the operator of the medical information processing apparatus 40 will be referred to as an image processing process A13a. Further, in the following sections, the medical image data I3 based on the image processing process A13a will be referred to as medical image data I33a.

More specifically, at first, the image interpreting doctor interprets the medical image data I13 while referencing the relevant image data I23 and the medical image data I33. In this situation, when having determined that there is relevant image data I2 that should be referenced besides the relevant image data I23, the image interpreting doctor requests a medical technologist to additionally acquire the relevant image data I2, for example. Alternatively, the image interpreting doctor himself operates the medical information processing apparatus 20 and additionally acquires the relevant image data I2. Further, the acquiring function 241 additionally acquires the relevant image data I23a in response to an input operation performed by the medical technologist or the image interpreting doctor and stores the additionally-acquired relevant image data I23a into the image storage circuitry 220.

Further, when having determined that there is medical image data I3 that should be referenced besides the medical image data I33, the image interpreting doctor requests a medical technologist to additionally perform the image processing process A13a based on the medical image data I13, for example. Alternatively, the image interpreting doctor himself operates the medical information processing apparatus 20 and additionally performs the image processing process A13a. Subsequently, in response to an input operation performed by the medical technologist or the image interpreting doctor, the image processing function 452 performs the image processing process A13a based on the medical image data I13. After that, the acquiring function 241 acquires the medical image data I33a based on the image processing process A13a from the medical information processing apparatus 40 and stores the acquired data into the image storage circuitry 220.

When the relevant image data I23a and/or the medical image data I33a were used for the interpretation of the medical image data I13, the evaluating function 242 determines that there was other image data used besides the relevant image data I23 and the medical image data I33. In that situation, the evaluating function 242 determines that the relevant image data I23 and the medical image data I33 correspond to "Insufficiency". In other words, the evaluating function 242 gives an evaluation "−2" to the relevant image data I23 and the image processing process A13 in accordance with whether or not there was other image data used for the interpretation of the medical image data I13 besides the relevant image data I23 and the medical image data I33.

Further, the evaluating function 242 judges whether or not a waiting time period was incurred by using the relevant image data I23 and the medical image data I33 during the interpretation of the medical image data I13. In this situation, the waiting time period may denote a time period from the time when the image interpreting doctor starts interpreting the images, to the time when the relevant image data I23 and the medical image data I33 become usable. For example, the waiting time period may denote the time period from the time when the image interpreting doctor starts up an image display application (a viewer) on the terminal device 50 for the purpose of interpreting the images, to the time when the relevant image data I23 and the medical image data I33 are displayed in the region R1 illustrated in FIG. 6.

In other words, there is a possibility, in some situations, that the acquisition of the relevant image data I23 and the medical image data I33 may not have been completed at the point in time when the image interpreting doctor intends to start interpreting the images, depending on the search method used at the time of acquiring the relevant image data I23 from the medical information processing apparatus 30 or parameter settings of the image processing process A13. In those situations, the evaluating function 242 determines that a waiting time period was incurred by using the relevant image data I23 and the medical image data I33 during the interpretation of the medical image data I13 and determines that the relevant image data I23 and the medical image data I33 correspond to "Delay". In other words, the evaluating function 242 gives an evaluation "−1" to the relevant image data I23 and the image processing process A13 in accordance with whether or not a waiting time period was incurred by using the relevant image data I23 and the medical image data I33 during the interpretation of the medical image data I13.

Further, when the relevant image data I23 and the medical image data I33 were each used for the interpretation of the medical image data I13, while there was no other image data used besides the relevant image data I23 and the medical image data I33, and no waiting time period was incurred by using the relevant image data I23 and the medical image data I33, the evaluating function 242 determines that the relevant image data I23 and the medical image data I33 correspond to "No Excess of Insufficiency". Further, the evaluating function 242 gives an evaluation "+2" to the relevant image data I23 and the image processing process A13.

As the examples of the evaluations, although FIG. 8 illustrates discrete values such as "+2", "+1", "−1", and "−2", possible embodiments are not limited to these examples. For instance, when having determined that the relevant image data I23 and the medical image data I33 correspond to "Excess", the evaluating function 242 may continuously increase or decrease the evaluation "+1" in accordance with the quantity of pieces of image data that were not used for the interpretation of the medical image data I13. As another example, when having determined that the relevant image data I23 and the medical image data I33 correspond to "Insufficiency", the evaluating function 242 may continuously increase or decrease the evaluation "−2" in accordance with the quantity of the other pieces of image data (e.g., the relevant image data I23a, the medical image data I33a, and the like) that were used besides the relevant image data I23 and the medical image data I33. Further, for example, when having determined that the relevant image data I23 and the medical image data I33 correspond to "Delay", the evaluating function 242 may continuously increase or decrease the evaluation "−1" in accordance with the length of the incurred waiting time period.

Further, the evaluating function 242 may further give the relevant image data I23 and the image processing process A13 an evaluation based on a result of the interpretation of the medical image data I13. More specifically, the evaluating function 242 may give an evaluation to the relevant image data I23 and the image processing process A13, in accordance with whether or not the image interpreting doctor was able to properly interpret the medical image data I13 by referencing the relevant image data I23 and the medical image data I33.

For example, the image interpreting doctor prepares an observation report by interpreting the medical image data I13, while referencing the relevant image data I23 and the medical image data I33. In this situation, the prepared observation report is normally double-checked by one or more other medical doctors or the like and is returned to the image interpreting doctor as a rejection, if there is any problem. Further, when the observation report is rejected and returned after being double-checked, the evaluating function 242 determines that the image interpreting doctor was not able to properly interpret the images and gives an evaluation "−1" to the relevant image data I23 and the image processing process A13.

Further, when the prepared observation report has an error, it is usually necessary to perform a re-examination. Further, when a re-examination became necessary, the evaluating function 242 determines that the image interpreting doctor was not able to properly interpret the images and gives an evaluation "−1" to the relevant image data I23 and the image processing process A13. On the contrary, when the observation report was not rejected after being double-checked, and also, no re-examination became necessary, the evaluating function 242 determines that the image interpreting doctor was able to properly interpret the images and gives an evaluation "+1" to the relevant image data I23 and the image processing process A13.

As for the evaluation based on the result of the interpretation of the medical image data I13, the evaluation may be added to the evaluation (an evaluation based on one of "No Excess or Insufficiency", "Excess", "Delay" and "Insufficiency") illustrated in FIG. 8.

In other words, the evaluating function 242 may calculate a total of the evaluation corresponding to one of "No Excess or Insufficiency", "Excess", "Delay", and "Insufficiency" and the evaluation based on the result of the image interpretation, so as to give the totaled evaluation to the relevant image data I23 and the image processing process A13.

Further, as explained above, the evaluating function 242 is configured to give an evaluation to the set made up of the relevant image data I23 and the image processing process A13, rather than individually giving an evaluation to the relevant image data I23 and to the image processing process A13. In other words, the evaluating function 242 is configured to give the evaluation to the series of workflow steps including the acquisition of the relevant image data I23 and the execution of the image processing process A13.

Subsequently, the specifying function 243 is configured to specify the input information input to the trained model M1 by the controlling function 245 and the evaluation given to the relevant image data I23 and the image processing process A13 by the evaluating function 242, as learning data for a trained model M2 (explained later). After that, the model generating function 244 is configured to generate the trained model M2 on the basis of the learning data specified by the specifying function 243. More specifically, the model generating function 244 generates the trained model M2 through reinforcement learning while using the learning data specified by the specifying function 243.

Even more specifically, as illustrated in FIG. 7, the model generating function 244 inputs the evaluation given to the relevant image data I23 and the image processing process A13 by the evaluating function 242, to the trained model M1. As a result, the trained model M1 learns a relationship between the input and the output so as to maximize the evaluation given to the output-side data, while using the input information including the medical image data I1 and the medical examination information T1 as the input-side data and using the relevant image data I2 and the image processing process A1 as the output-side data. In other words, the model generating function 244 generates the trained model M2 by optimizing the trained model M1 through the reinforcement learning that uses the evaluation given to the relevant image data I23 and the image processing process A13 by the evaluating function 242 as a "reward". Similarly to the trained model M1, the trained model M2 is provided with a function to specify relevant image data I2 and an image processing process A1 on the basis of the input information including the medical image data I1 and the medical examination information T1. Further, the model generating function 244 stores the generated trained model M2 into the model storage circuitry 230.

When the medical image diagnosis apparatus 10 has further acquired medical image data I14 after the trained model M2 is stored in the model storage circuitry 230, the acquiring function 241 acquires the medical image data I14 from the medical image diagnosis apparatus 10 and stores the acquired data into the image storage circuitry 220. Subsequently, the controlling function 245 reads the trained model M2 from the model storage circuitry 230 and causes the trained model M2 to specify, on the basis of input information including the medical image data I14 and medical examination information T14 related to the medical image data I14, relevant image data (hereinafter, "relevant image data I24") relevant to the medical image data I14 and an image processing process (hereinafter, "image processing process A14") performed on the basis of the medical image data I14. In this situation, the medical image data I14 is an example of the medical image data I1. Further, the medical examination information T14 is an example of the medical examination information T1. The relevant image data I24 is an example of the relevant image data I2. Also, the image processing process A14 is an example of the image processing process A1.

Subsequently, the acquiring function 241 acquires the relevant image data I24 specified by the trained model M2 from the medical information processing apparatus 30 and stores the acquired data into the image storage circuitry 220. Further, the output function 246 outputs the medical image data I14 to the medical information processing apparatus 40. After that, the image processing function 452 of the medical information processing apparatus 40 performs the image processing process A14 specified by the trained model M2, on the basis of the medical image data I14. Subsequently, the acquiring function 241 acquires medical image data I14 (hereinafter "medical image data I34") resulting from the image processing process A14, from the medical information processing apparatus 40 and stores the acquired data into the image storage circuitry 220. In this situation, the medical image data I34 is an example of the medical image data I3.

Subsequently, the display controlling function 542 of the terminal device 50 causes the display 520 to display the medical image data I14 acquired by the acquiring function 241. Further, the display controlling function 542 causes the display 520 to display the relevant image data I24 and the medical image data I34 acquired by the acquiring function 241. More specifically, in response to an input operation performed by the image interpreting doctor, the display controlling function 542 requests the image data from the medical information processing apparatus 20. Subsequently, from among the pieces of image data (the medical image data I14, the relevant image data I24, the medical image data I34, and the like) stored in the image storage circuitry 220, the output function 246 outputs the image data corresponding to the request to the terminal device 50. After that, the display controlling function 542 receives the image data output by the output function 246 and causes the display 520 to display the received image data. Subsequently, the image interpreting doctor interprets the medical image data I14 while referencing the relevant image data I24 and the medical image data I34, so as to prepare an observation report.

As explained above, the medical information processing apparatus 20 is configured to specify the relevant image data I24 and the image processing process A14 by using the trained model M2. In other words, by using the medical information processing apparatus 20, it is possible to simplify the workflow from the acquisition to the interpretation of the medical image data I14 by automating the acquisition of the relevant image data I24 and the image processing process A14 based on the medical image data I14.

Further, the trained model M2 is generated through the reinforcement learning that uses, as the learning data, the input information including the medical image data I1 and the medical examination information T1, as well as the evaluation given to the relevant image data I2 and the image processing process A1. Accordingly, by using the trained model M2, the medical information processing apparatus 20 is able to properly provide the relevant image data I2 and the medical image data I3, while avoiding: excessively performing the acquisition of the relevant image data I2 and the execution of the image processing process A1; having insufficiency in the acquisition of the relevant image data I2 and the execution of the image processing process A1; and incurring a waiting time period for the acquisition of the relevant image data I2 and the execution of the image processing process A1.

Further, the evaluating function 242 is configured to give the evaluation to the relevant image data I24 and the image processing process A14 specified by the trained model M2. Subsequently, the specifying function 243 is configured to specify the input information input to the trained model M2 by the controlling function 245 and the evaluation given to the relevant image data I24 and the image processing process A14 by the evaluating function 242 as the learning data for the trained model M2. After that, the model generating function 244 is configured to re-generate the trained model M2, on the basis of the learning data specified by the specifying function 243. In other words, the model generating function 244 is configured to update the trained model M2 every time the workflow from the acquisition to the interpretation of the medical image data I1 is carried out. As a result, the medical information processing apparatus 20 is able to properly provide the relevant image data I2 and the medical image data I3, by gradually enhancing the level of precision of the trained model M2.

Figure 9:
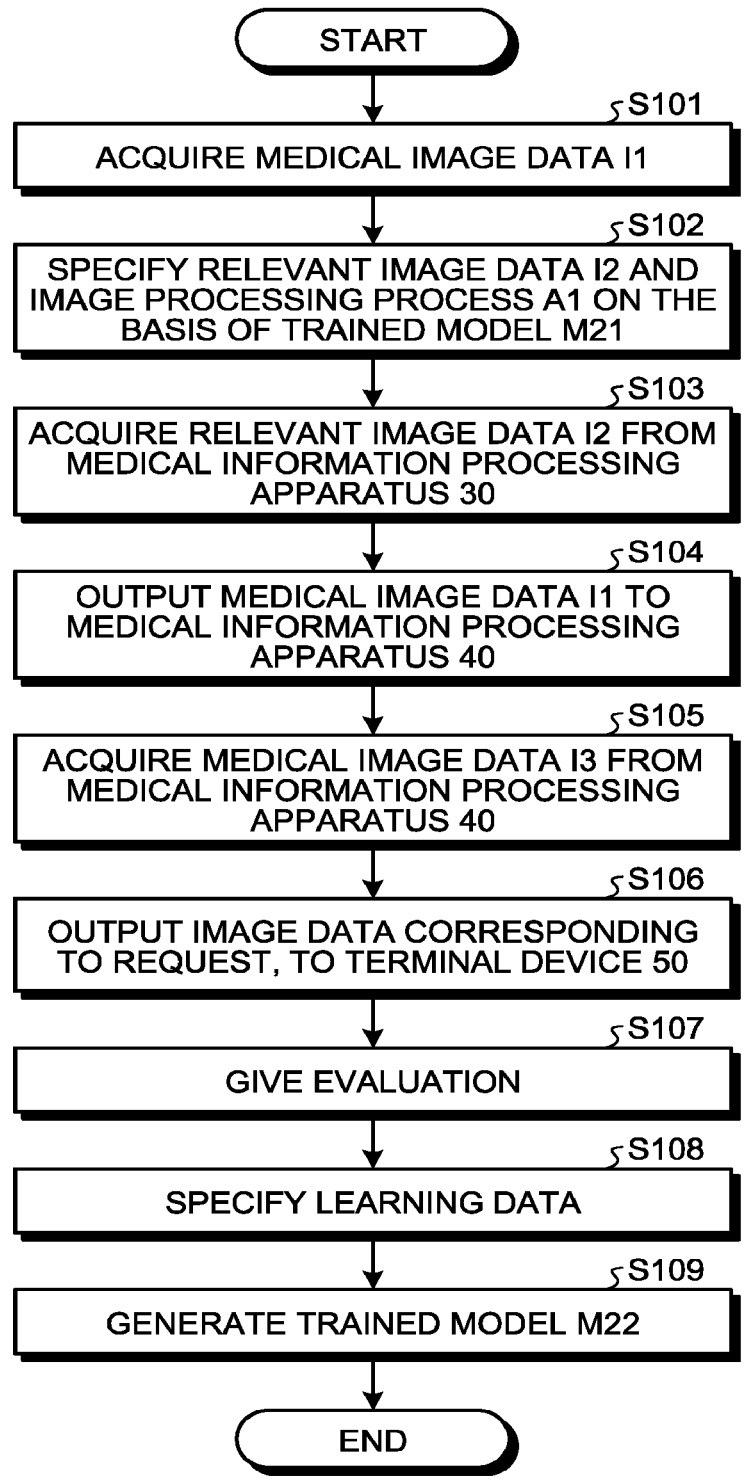
FIG. 9 is a flowchart for explaining a flow in a series of processes performed by the medical information processing apparatus according to the first embodiment.

Next, an example of a procedure in processes performed by the medical information processing apparatus 20 will be explained, with reference to FIG. 9. FIG. 9 is a flowchart for explaining a flow in a series of processes performed by the medical information processing apparatus 20 according to the first embodiment. Steps S101, S103, S105, and S106 are steps corresponding to the acquiring function 241. Step S107 is a step corresponding to the evaluating function 242. Step S108 is a step corresponding to the specifying function 243. Step S109 is a step corresponding to the model generating function 244. Step S102 is a step corresponding to the controlling function 245. Step S104 is a step corresponding to the output function 246. With reference to FIG. 9, a trained model M21 and another trained model M22 will be explained as examples of the trained model M2.

At first, the processing circuitry 240 acquires medical image data I1 from the medical image diagnosis apparatus 10 and stores the acquired data into the image storage circuitry 220 (step S101). Subsequently, the processing circuitry 240 reads the trained model M21 stored in the model storage circuitry 230 and causes the trained model M21 to specify relevant image data I2 relevant to the medical image data I1 and an image processing process A1 performed on the basis of the medical image data I1, on the basis of the input information including the medical image data I1 and medical examination information T1 (step S102).

After that, the processing circuitry 240 acquires the relevant image data I2 specified by the trained model M21, from the medical information processing apparatus 30 (step S103). Subsequently, the processing circuitry 240 outputs the medical image data I1 to the medical information processing apparatus 40 (step S104). In this situation, the image processing function 452 of the medical information processing apparatus 40 performs the image processing process A1 specified by the trained model M21, on the basis of the medical image data I1. Further, the processing circuitry 240 acquires the medical image data I1 (medical image data I3) resulting from the image processing process A1 from the medical information processing apparatus 40 (step S105). In this situation, the order by which the step S103 and steps S104 and S105 are performed is arbitrary, and it is also acceptable to perform these steps parallel to each other.

After that, the processing circuitry 240 outputs image data corresponding to the request from the terminal device 50 to the terminal device 50 (step S106). As a result, the display controlling function 542 of the terminal device 50 causes the display 520 to display the medical image data I1, the relevant image data I2, and the medical image data I3. Further, the image interpreting doctor interprets the medical image data I1 while referencing the relevant image data I2 and the medical image data I3, so as to prepare an observation report.

Subsequently, the processing circuitry 240 gives an evaluation to the relevant image data I2 and the image processing process A1 specified by the trained model M21 on the basis of the input information (step S107). After that, the processing circuitry 240 specifies the input information and the evaluation as learning data (step S108). Subsequently, the processing circuitry 240 generates the trained model M22 on the basis of the specified learning data (step S109). In other words, the processing circuitry 240 updates the trained model M2 on the basis of the learning data. After that, the generated trained model M22 is stored into the model storage circuitry 230, and the process is subsequently ended.

The example was explained in which, at step S102 in FIG. 9, the relevant image data I2 and the image processing process A1 are specified on the basis of the trained model M2 generated through the reinforcement learning; however, it is also acceptable to use a trained model other than the trained model M2 at step S102. For example, the processing circuitry 240 may, at step S102, specify relevant image data I2 and an image processing process A1 on the basis of the trained model M1 generated through supervised learning.

As explained above, according to the first embodiment, the evaluating function 242 is configured to give the evaluation to the relevant image data I2 and the image processing process A1 specified by one of the trained models M1 and M2 on the basis of the input information. Further, the specifying function 243 is configured to specify the input information and the evaluation as the learning data for the trained model M2. Accordingly, the medical information processing apparatus 20 according to the first embodiment is able to improve the workflow from the acquisition to the interpretation of the medical image data I1.

In other words, by using the learning data specified by the specifying function 243, the model generating function 244 is able to generate the trained model M2, and the controlling function 245 is able to cause the trained model M2 to specify the relevant image data I2 and the image processing process A1. The medical information processing apparatus 20 is therefore able to simplify the workflow from the acquisition to the interpretation of the medical image data I1, by automating the acquisition of the relevant image data I2 and the image processing process A1 based on the medical image data I1.

Further, by using the learning data specified by the specifying function 243, the model generating function 244 is able to generate the trained model M2 through the reinforcement learning that uses the input information and the evaluation as the learning data. The medical information processing apparatus 20 is therefore able to enhance the level of precision of the relevant image data I2 and the image processing process A1 specified by the trained model M2 and to properly provide the relevant image data I2 and the medical image data I3 for the interpretation of the medical image data I1.

Further, as explained above, according to the first embodiment, the evaluating function 242 is configured to give the evaluation in accordance with whether or not the relevant image data I2 specified by one of the trained models M1 and M2 and the medical image data I3 based on the image processing process A1 specified by one of the trained models M1 and M2 were each used for the interpretation of the medical image data I1. Accordingly, the medical information processing apparatus 20 is able to properly provide the relevant image data I2 and the medical image data I3 by causing the trained model M2 to learn so as to avoid excessive acquisition of the relevant image data I2 and excessive execution of the image processing process A1.

Further, as explained above, according to the first embodiment, the evaluating function 242 is configured to give the evaluation in accordance with whether or not there was other image data used for the interpretation of the medical image data I1, besides the relevant image data I2 specified by one of the trained models M1 and M2 and the medical image data I3 based on the image processing process A1 specified by one of the trained models M1 and M2. Accordingly, the medical information processing apparatus 20 is able to properly provide the relevant image data I2 and the medical image data I3, by causing the trained model M2 to learn so that there is no insufficiency with respect to the acquisition of the relevant image data I2 and the image processing process A1.

Further, as explained above, according to the first embodiment, the evaluating function 242 is configured to give the evaluation in accordance with whether or not a waiting time period was incurred by using the relevant image data I2 specified by one of the trained models M1 and M2 and the medical image data I3 based on the image processing process A1 specified by one of the trained models M1 and M2, during the interpretation of the medical image data I1. Accordingly, the medical information processing apparatus 20 is able to properly provide the relevant image data I2 and the medical image data I3 by causing the trained model M2 to learn so that no waiting time period is incurred for the image interpreting doctor.

The first embodiment has thus been explained. It is also possible to carry out the present disclosure in various different modes other than those described in the first embodiment.

In the embodiments described above, the example was explained in which the acquiring function 241 is configured to acquire the relevant image data I2 from the medical information processing apparatus 30; however, possible embodiments are not limited to this example. For instance, when the image storage circuitry 220 is storage having a plurality of hierarchical layers, the acquiring function 241 may acquire the relevant image data I2 specified by one of the trained models M1 and M2 from a low-speed hierarchical layer of the image storage circuitry 220 and store the acquired data into a high-speed hierarchical layer of the image storage circuitry 220.

In the following sections an example will be explained in which the image storage circuitry 220 is storage having a high-speed hierarchical layer H1 and a low-speed hierarchical layer H2. The high-speed hierarchical layer H1 is realized by using a Solid State Drive (SSD), for example. In contrast, the low-speed hierarchical layer is realized by using a Hard Disk Drive, (HDD), for example. It is possible to input and output data to and from the hierarchical layer H1 at a speed higher than that of the hierarchical layer H2. In contrast, the hierarchical layer H2 has a lower cost per data amount than the hierarchical layer H1 and is usually structured to have a larger capacity than that of the hierarchical layer H1.

For example, image data scheduled to be used for image interpretation or the like is stored in the hierarchical layer H1. For example, when the medical image data I1 is acquired from the patient P1 by the medical image diagnosis apparatus 10, the acquiring function 241 acquires the medical image data I1 from the medical image diagnosis apparatus 10 and stores the acquired data into the hierarchical layer H1 of the image storage circuitry 220. In contrast, image data acquired in the past from the patient P1 and image data acquired in the past from the patient P2 different from the patient P1 are stored in the hierarchical layer H2.

In this situation, it takes a while to read the image data stored in the low-speed hierarchical layer H2 and causes the terminal device 50 to display the image data. In other words, when the image interpreting doctor operating the terminal device 50 intends to reference the image data stored in the low-speed hierarchical layer H2, a waiting time period might be incurred for the image interpreting doctor.

To cope with this situation, the acquiring function 241 moves, in advance, image data having a possibility of being referenced by the image interpreting doctor, from the low-speed hierarchical layer H2 to the high-speed hierarchical layer H1. In other words, the acquiring function 241 prefetches the image data having a possibility of being referenced by the image interpreting doctor. More specifically, the acquiring function 241 acquires the relevant image data I2 specified by one of the trained models M1 and M2 from the low-speed hierarchical level H2 and stores the acquired data into the high-speed hierarchical layer H1. As a result, the medical information processing apparatus 20 is able to avoid the situation where a waiting time period for the image interpreting doctor is incurred by using the relevant image data I2 for the interpretation of the medical image data I1.

Further, in the embodiments described above, the example was explained in which the evaluation is given to the relevant image and the image processing process; however, possible embodiments are not limited to this example.

For instance, the evaluating function 242 may omit giving an evaluation to the image processing process and may give an evaluation only to the relevant image. In one example, the controlling function 245 at first causes one of the trained models M1 and M2 to specify the relevant image data I2 on the basis of the input information. Further, the evaluating function 242 gives an evaluation to the specified relevant image data I2. After that, the specifying function 243 specifies the input information and the evaluation given to the relevant image data I2 as learning data for the trained model M2. Subsequently, the model generating function 244 generates a trained model M2 on the basis of the learning data. After that, the acquiring function 241 acquires medical image data I1 from the medical image diagnosis apparatus 10. Further, the controlling function 245 causes the trained model M2 generated by the model generating function 244 to specify relevant image data I2, on the basis of the input information including the medical image data I1 and medical examination information T1. In this situation, the controlling function 245 is able to specify an image processing process A1 on the basis of conditions and/or rules that are preset or to specify an image processing process A1 on the basis of an input operation performed by the operator.

Further, for example, the evaluating function 242 may omit giving an evaluation to the relevant image and may give an evaluation only to the image processing process. In one example, the controlling function 245 at first causes one of the trained models M1 and M2 to specify an image processing process A1 on the basis of the input information. Further, the evaluating function 242 gives an evaluation to the specified image processing process A1. Further, the specifying function 243 specifies the input information and the evaluation given to the image processing process A1 as learning data for the trained model M2. Subsequently, the model generating function 244 generates a trained model M2 on the basis of the learning data. After that, the acquiring function 241 acquires medical image data I1 from the medical image diagnosis apparatus 10. Subsequently, the controlling function 245 causes the trained model M2 generated by the model generating function 244 to specify an image processing process A1 on the basis of input information including the medical image data I1 and medical examination information T1. In this situation, the controlling function 245 is able to specify relevant image data I2 on the basis of conditions and/or rules that are preset or to specify relevant image data I2 on the basis of an input operation performed by the operator.

Further, in the embodiments above, the example was explained in which the processing circuitry 240 of the medical information processing apparatus 20 includes the acquiring function 241, the evaluating function 242, the specifying function 243, the model generating function 244, the controlling function 245, and the output function 246; however, it is possible to provide these functions in a plurality of apparatuses in a distributed manner as appropriate.

For example, the medical information processing system 1 may further include a medical information processing apparatus 60 (not illustrated). Further, the medical information processing apparatus 60 includes processing circuitry 610 (not illustrated). The processing circuitry 610 is configured to execute a function (hereinafter "model generating function 611") corresponding to the model generating function 244. In that situation, the evaluating function 242 is configured to give an evaluation to the relevant image data I2 and the image processing process A1 specified by one of the trained models M1 and M2 on the basis of the input information. Further, the specifying function 243 is configured to specify the input information and the evaluation as learning data for the trained model M2. Subsequently, the output function 246 is configured to output the learning data specified by the specifying function 243 to the medical information processing apparatus 60. After that, the model generating function 611 of the medical information processing apparatus 60 is configured to generate a trained model M2 on the basis of the learning data and to output the generated trained model M2 to the medical information processing apparatus 20. Subsequently, the acquiring function 241 is configured to acquire medical image data I1 from the medical image diagnosis apparatus 10. After that, the controlling function 245 is configured to cause the trained model M2 generated by the model generating function 611 to specify relevant image data I2 and an image processing process A1 on the basis of input information including the medical image data I1 and medical examination information T1.

In another example, the medical information processing system 1 may further include a medical information processing apparatus 70 (not illustrated). The medical information processing apparatus 70 includes processing circuitry 710 (not illustrated) and model storage circuitry 720 corresponding to the model storage circuitry 230. Further, the processing circuitry 710 is configured to execute a function (hereinafter, "controlling function 711") corresponding to the controlling function 245. In that situation, the acquiring function 241 is configured to acquire the medical image data I1 from the medical image diagnosis apparatus 10. Subsequently, the output function 246 is configured to output the medical image data I1 and the medical examination information T1 related to the medical image data I1 to the medical information processing apparatus 70. After that, the controlling function 711 of the medical information processing apparatus 70 is configured to cause the trained model M2 stored in the model storage circuitry 720 to specify relevant image data I2 and an image processing process A1, on the basis of the input information including the medical image data I1 and the medical examination information T1. Further, the acquiring function 241 is configured to acquire relevant image data I2 specified by the trained model M2 and to store the acquired data into the image storage circuitry 220. Further, the image processing function 452 is configured to perform the image processing process A1 specified by the trained model M2, on the basis of the medical image data I1.

The constituent elements of the apparatuses and the devices described in the embodiments above are based on functional concepts. Thus, it is not necessary to physically configure the constituent elements as indicated in the drawings. In other words, specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a program analyzed and executed by the CPU or may be realized as hardware using wired logic.

It is possible to realize the processing method described in any of the embodiments above by causing a computer such as a personal computer or a workstation to execute a program prepared in advance. It is possible to distribute the program via a network such as the Internet. Further, it is also possible to record the program onto a computer-readable non-transitory recording medium such as a hard disk, a flexible disk (FD), a Compact Disk Read-Only Memory (CD-ROM), a Magneto Optical (MO) disk, a Digital Versatile Disk (DVD), or the like, so as to be executed as being read from the recording medium by a computer.

According to at least one aspect of the embodiments described above, it is possible to improve the workflow from the acquisition to the interpretation of the medical images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus, comprising:
a memory storing therein a trained model provided with a function to determine and output, based on input information including a medical image and medical examination information related to the medical image, a relevant image relevant to the medical image and an image processing process performed based on the medical image; and
processing circuitry configured to determine an evaluation value of a combination of a particular relevant image and a particular image processing process determined and output by the trained model, wherein the evaluation value is a rating of the combination of the particular relevant image and the particular image processing process with respect to interpretation of the medical image.

2. The medical information processing apparatus according to claim 1, wherein the processing circuitry is further configured to specify the input information and the evaluation value as learning data for the trained model.

3. The medical information processing apparatus according to claim 2, wherein the processing circuitry is further configured to generate the trained model based on the learning data.

4. The medical information processing apparatus according to claim 1, wherein the processing circuitry is further configured to update the trained model based on the input information and the evaluation value.

5. The medical information processing apparatus according to claim 1, wherein the processing circuitry is further configured to determine the evaluation value in accordance with whether or not the particular relevant image determined by the trained model and a particular medical image resulting from the image processing process determined by the trained model were each used for the interpretation of the medical image.

6. The medical information processing apparatus according to claim 1, wherein the processing circuitry is further configured to determine the evaluation value in accordance with whether or not there was one or more other images used for the interpretation of the medical image, besides the particular relevant image determined by the trained model and a particular medical image resulting from the particular image processing process determined by the trained model.

7. The medical information processing apparatus according to claim 1, wherein the processing circuitry is further configured to determine the evaluation value in accordance with whether or not a waiting time period was incurred by using the particular relevant image determined by the trained model and a particular medical image resulting from the particular image processing process determined by the trained model, during the interpretation of the medical image.

8. The medical information processing apparatus according to claim 1, wherein the processing circuitry is further configured to determine the evaluation value based on a result of the interpretation of the medical image.

9. The medical information processing apparatus according to claim 1, wherein the processing circuitry is further configured to acquire the particular relevant image determined by the trained model and a particular medical image resulting from the particular image processing process determined by the trained model, and store the acquired particular relevant image and the particular medical image into an image memory.

10. The medical information processing apparatus according to claim 9, wherein
the image memory is storage having a plurality of hierarchical layers, and
the processing circuitry is further configured to acquire the particular relevant image determined by the trained model from a low-speed hierarchical layer in the image memory, and store the acquired particular relevant image into a high-speed hierarchical layer in the image memory.

11. The medical information processing apparatus according to claim 1, wherein the processing circuitry is further configured to cause the trained model to determine the particular relevant image and the particular image processing process, based on the input information.

12. The medical information processing apparatus according to claim 11, wherein the processing circuitry is further configured to cause the trained model to determine the particular relevant image and the particular image processing process, by using additional information of the medical image as the medical examination information.

13. The medical information processing apparatus according to claim 11, wherein the processing circuitry is further configured to cause the trained model to determine the particular relevant image and the particular image processing process, by using order information used at a time of acquiring the medical image as the medical examination information.

14. The medical information processing apparatus according to claim 11, wherein the processing circuitry is further configured to cause the trained model to determine, as the particular relevant image, an image of a patient who is a same patient as a patient imaged in the medical image.

15. The medical information processing apparatus according to claim 11, wherein the processing circuitry is further configured to cause the trained model to determine, as the particular relevant image, an image of a patient having a clinical case that is a same clinical case as or similar to that of a patient imaged in the medical image.

16. The medical information processing apparatus according to claim 11, the processing circuitry is further configured to cause the trained model to determine, as the particular image processing process, a process of generating a three-dimensional image based on the medical image that is two-dimensional, and generating a two-dimensional image based on the three-dimensional image.

17. The medical information processing apparatus according to claim 11, wherein the processing circuitry is further configured to cause the trained model to determine, as the particular image processing process, an analyzing process performed based on the medical image.

18. A medical information processing system, comprising:
   a memory storing therein a trained model provided with a function to determine and output, based on input information including a medical image and medical examination information related to the medical image, a relevant image relevant to the medical image and an image processing process performed based on the medical image; and
   processing circuitry configured to:
      cause the trained model to determine and output a particular relevant image and a particular image processing process based on the input information;
      perform the particular image processing process determined and output by the trained model based on the medical image;
      acquire the particular relevant image determined by the trained model and a particular medical image resulting from the particular image processing process determined by the trained model, and store the acquired particular relevant image and particular medical image into an image memory;
      cause the particular relevant image stored in the image memory and the particular medical image resulting from the particular image processing process determined by the trained model to be displayed;
      determine an evaluation value of a combination of the particular relevant image stored in the image memory and the particular image processing process determined by the trained model, wherein the evaluation value is a rating of the combination of the particular relevant image and the particular image processing process with respect to interpretation of the medical image; and
      specify the input information and the determined evaluation score as learning data for the trained model.

* * * * *